(12) United States Patent
Linderman et al.

(10) Patent No.: US 8,128,633 B2
(45) Date of Patent: Mar. 6, 2012

(54) DEVICE, SYSTEM, AND METHOD FOR FORMING A CAVITY IN AND DELIVERING A CURABLE MATERIAL INTO BONE

(75) Inventors: Evan D. Linderman, Northbrook, IL (US); John A. Krueger, Muskego, WI (US)

(73) Assignee: CareFusion 2200, Inc., San Diego, CA (US)

( * ) Notice: Subject to any disclaimer, the term of this patent is extended or adjusted under 35 U.S.C. 154(b) by 154 days.

(21) Appl. No.: 12/634,366

(22) Filed: Dec. 9, 2009

(65) Prior Publication Data

US 2010/0121336 A1    May 13, 2010

Related U.S. Application Data

(63) Continuation-in-part of application No. 11/704,139, filed on Feb. 8, 2007, now Pat. No. 7,799,035, which is a continuation-in-part of application No. 11/282,102, filed on Nov. 18, 2005, now Pat. No. 7,713,273.

(51) Int. Cl.
*A61B 17/56* (2006.01)
*A61M 25/00* (2006.01)

(52) U.S. Cl. .......................... 606/94; 604/264

(58) Field of Classification Search ............ 606/94, 606/264, 93, 92, 185; 604/272, 164.01, 506, 604/164.11, 187, 95.01, 82, 264; 433/224; 222/386.5, 399
See application file for complete search history.

(56) References Cited

U.S. PATENT DOCUMENTS

| | | |
|---|---|---|
| 4,265,231 A | 5/1981 | Scheller, Jr. et al. |
| 4,518,383 A * | 5/1985 | Evans ..................... 604/512 |
| 5,295,980 A | 3/1994 | Ersek |
| 5,609,629 A | 3/1997 | Fearnot et al. |
| 5,732,698 A | 3/1998 | Swanson et al. |
| 5,843,103 A | 12/1998 | Wulfman |
| 5,851,209 A | 12/1998 | Kummer et al. |
| 5,879,353 A | 3/1999 | Terry |
| 5,891,147 A | 4/1999 | Moskovitz et al. |
| 5,928,239 A | 7/1999 | Mirza |
| 5,972,015 A | 10/1999 | Scribner et al. |
| 6,048,346 A | 4/2000 | Reiley et al. |
| 6,066,154 A | 5/2000 | Reiley et al. |
| 6,241,734 B1 | 6/2001 | Scribner et al. |
| 6,248,110 B1 | 6/2001 | Reiley et al. |

(Continued)

FOREIGN PATENT DOCUMENTS

EP    1459691 A1    9/2004

(Continued)

*Primary Examiner* — Pedro Philogene
(74) *Attorney, Agent, or Firm* — Brinks Hofer Gilson & Lione

(57) ABSTRACT

A curable material delivery cannula device is disclosed. The device includes a cannula and a hub. The cannula includes an open proximal end, a deflectable segment forming a pre-set curve, a lumen, and side orifice(s) adjacent, and proximally spaced from, the distal end and fluidly connected to the lumen. When inserted within a guide cannula, the deflectable segment straightens. When distally extended from the guide cannula, the deflectable segment reverts to the curved shape. The distal end has a blunt tip for non-traumatic interface with bodily material. During use, curable material, such as bone cement, is delivered from the side orifice(s) in a radial direction relative to the lumen. The device may be used to create voids for receiving curable material, and may include spacers configured to control location and/or orientation of the voids.

20 Claims, 21 Drawing Sheets

U.S. PATENT DOCUMENTS

| | | | |
|---|---|---|---|
| 6,296,639 B1 | 10/2001 | Truckai et al. | |
| 6,328,744 B1 | 12/2001 | Harari et al. | |
| 6,358,251 B1 | 3/2002 | Mirza | |
| 6,383,188 B2 | 5/2002 | Kuslich et al. | |
| 6,383,190 B1 | 5/2002 | Preissman | |
| 6,425,887 B1 | 7/2002 | McGuckin et al. | |
| 6,440,138 B1 | 8/2002 | Reiley et al. | |
| 6,494,868 B2 | 12/2002 | Amar | |
| 6,575,978 B2 | 6/2003 | Peterson et al. | |
| 6,592,559 B1 * | 7/2003 | Pakter et al. | 604/272 |
| 6,641,587 B2 | 11/2003 | Scribner et al. | |
| 6,645,213 B2 * | 11/2003 | Sand et al. | 606/92 |
| 6,676,664 B1 | 1/2004 | Al Assir | |
| 6,679,886 B2 | 1/2004 | Weikel et al. | |
| 6,740,090 B1 | 5/2004 | Cragg et al. | |
| 6,746,451 B2 | 6/2004 | Middleton et al. | |
| 6,783,515 B1 | 8/2004 | Miller et al. | |
| 6,790,210 B1 | 9/2004 | Cragg et al. | |
| 6,793,660 B2 | 9/2004 | Kerr et al. | |
| 6,814,734 B2 | 11/2004 | Chappuis et al. | |
| 6,843,796 B2 | 1/2005 | Harari et al. | |
| 6,863,672 B2 | 3/2005 | Reiley et al. | |
| 6,875,219 B2 * | 4/2005 | Arramon et al. | 606/92 |
| 6,921,403 B2 | 7/2005 | Cragg et al. | |
| 6,923,813 B2 | 8/2005 | Phillips et al. | |
| 7,004,945 B2 | 2/2006 | Boyd et al. | |
| 7,025,771 B2 | 4/2006 | Kuslich et al. | |
| 7,048,743 B2 | 5/2006 | Miller et al. | |
| 7,066,942 B2 | 6/2006 | Treace | |
| 7,087,040 B2 | 8/2006 | McGuckin, Jr. et al. | |
| 7,087,058 B2 | 8/2006 | Cragg | |
| 7,114,501 B2 | 10/2006 | Johnson et al. | |
| 7,850,651 B2 * | 12/2010 | Allee et al. | 604/164.01 |
| 7,972,312 B2 * | 7/2011 | Koopman | 604/187 |
| 2002/0099384 A1 | 7/2002 | Scribner et al. | |
| 2002/0120240 A1 | 8/2002 | Bagga et al. | |
| 2002/0156483 A1 | 10/2002 | Voellmicke et al. | |
| 2003/0036762 A1 | 2/2003 | Kerr et al. | |
| 2003/0078589 A1 | 4/2003 | Preissman | |
| 2004/0068264 A1 | 4/2004 | Treace | |
| 2004/0068267 A1 | 4/2004 | Harvie et al. | |
| 2004/0162559 A1 | 8/2004 | Arramon et al. | |
| 2004/0215202 A1 | 10/2004 | Preissman | |
| 2005/0038432 A1 | 2/2005 | Shaolian et al. | |
| 2005/0070913 A1 | 3/2005 | Milbocker et al. | |
| 2006/0009779 A1 | 1/2006 | Collins et al. | |
| 2006/0064101 A1 | 3/2006 | Arramon | |
| 2006/0116643 A1 | 6/2006 | Dixon | |
| 2006/0149280 A1 | 7/2006 | Harvie et al. | |
| 2006/0195094 A1 | 8/2006 | McGraw et al. | |
| 2006/0217736 A1 | 9/2006 | Kaneko et al. | |
| 2006/0241624 A1 | 10/2006 | Kizuka et al. | |
| 2006/0264967 A1 | 11/2006 | Ferreyro et al. | |

FOREIGN PATENT DOCUMENTS

WO     WO 98/56301 A1     12/1998

* cited by examiner

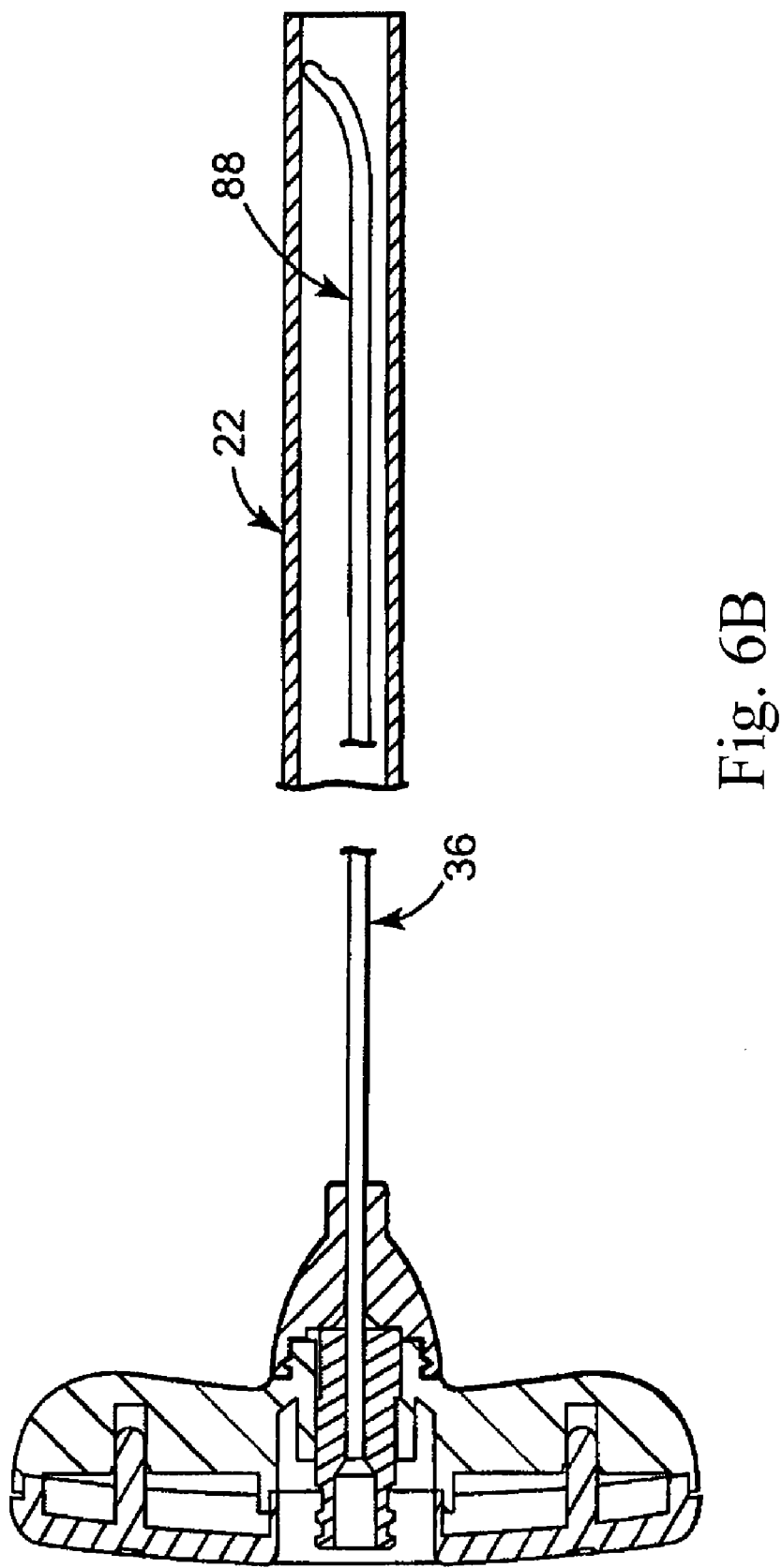

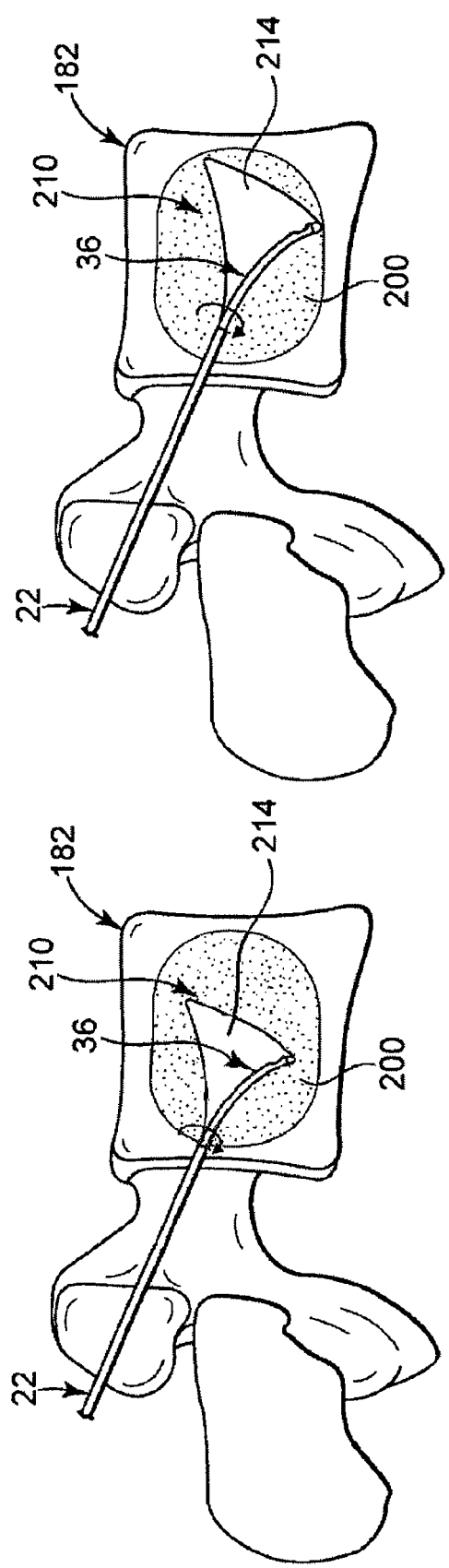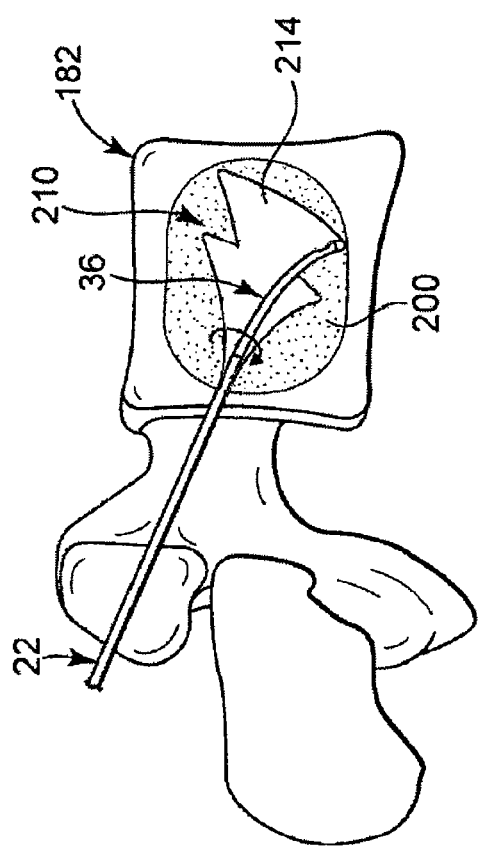
Fig. 10A
Fig. 10B
Fig. 10C

DEVICE, SYSTEM, AND METHOD FOR FORMING A CAVITY IN AND DELIVERING A CURABLE MATERIAL INTO BONE

RELATED APPLICATIONS

This application is a continuation-in-part of pending U.S. patent application Ser. No. 11/704,139, entitled "Device, System and Method for Delivering a Curable Material Into Bone," filed Feb. 8, 2007, which is a continuation-in-part of U.S. patent application Ser. No. 11/282,102, entitled "Device, System and Method for Delivering a Curable Material Into Bone," filed Nov. 18, 2005, each of which is herein incorporated by reference in its entirety.

BACKGROUND

The present invention relates to devices and methods for stabilizing bone structures. More particularly, it relates to devices, systems and methods for delivering a curable, stabilizing material into a bone structure.

Surgical intervention at damaged or compromised bone sites has proven highly beneficial for patients, for example patients with back pain associated with vertebral damage.

Bones of the human skeletal system include mineralized tissue that can generally be categorized into two morphological groups: "cortical" bone and "cancellous" bone. Outer walls of all bones are composed of cortical bone, which has a dense, compact bone structure characterized by a microscopic porosity. Cancellous or "trabecular" bone forms the interior structure of bones. Cancellous bone is composed of a lattice of interconnected slender rods and plates known by the term "trabeculae."

During certain bone procedures, cancellous bone is supplemented by an injection of a palliative (or curative) material employed to stabilize the trabeculae. For example, superior and inferior vertebrae in the spine can be beneficially stabilized by the injection of an appropriate, curable material (e.g., PMMA or other bone cement). In other procedures, percutaneous injection of stabilization material into vertebral compression fractures by, for example, transpedicular or parapedicular approaches, has proven beneficial in relieving pain and stabilizing damaged bone sites. Other skeletal bones (e.g., the femur) can be treated in a similar fashion. In any regard, bone in general, and cancellous bone in particular, can be strengthened and stabilized by a palliative injection of bone-compatible material.

The conventional technique for delivering the bone stabilizing material entails employment of a straight access device or cannula that bores (or otherwise cuts) through the cortical bone to gain access to the cancellous bone site. Bone stabilization material is then driven through the cannula to fill a portion of the cancellous bone at the bone site. To minimize invasiveness of the procedure, the cannula is typically a small diameter needle.

With the above in mind, because the needle cannula interacts with the cancellous bone and other soft tissue structures, an inherent risk exists that following initial insertion, the needle cannula might core or puncture other tissue and/or the bone mass being repaired (at a location apart from the insertion site). Thus, during percutaneous vertebroplasty, great care must be taken to avoid puncturing, coring, or otherwise rupturing the vertebral body. Similar post-insertion coring concerns arise in other interior bone repair procedures. Along these same lines, to minimize trauma and time required to complete the procedure, it is desirable that only a single bone site insertion be performed. Unfortunately, for many procedures, the surgical site in question cannot be fully accessed using a conventional, straight needle cannula. For example, with vertebroplasty, the confined nature of the inner vertebral body oftentimes requires two or more insertions with the straight needle cannula at different vertebral approach locations ("bipedicular" technique). It would be desirable to provide a system for delivering bone stabilizing material that can more readily adopt to the anatomical requirements of a particular delivery site, for example a system capable of promoting unipedicular vertebroplasty.

Certain currently-available instruments utilize a curved needle to deliver bone stabilizing material as part of vertebroplasty or similar procedure. The curved needle purportedly enhances a surgeon's ability to locate and inject the stabilizing material at a desired site. Similar to a conventional straight needle cannula, the curved needle dispenses the curable material through a single, axial opening at the distal-most tip. However, the curved needle is used in combination with an outer cannula that assists in generally establishing access to the bone site as well as facilitating percutaneous delivery of the needle to the delivery site (within bone) in a desired fashion. More particularly, the outer cannula first gains access to the bone site, followed by distal sliding of the needle through the outer cannula.

After the needle's tip extends distal a distal end of the outer cannula, the needle tip is "exposed" relative to the bone site. To avoid coring, and thus potentially damaging, tissue when inserting the needle's distal tip into the bone site, an additional wire component is required, coaxially disposed within the needle and distally extending from the distal tip. The inner wire "protects" tissue or other bodily structures from traumatically contacting the distal tip of the needle as the tip is being positioned. The coaxial wire must be removed prior to infusing the bone stabilizing material through the needle. Further, the needle can only dispense the stabilizing material through the axial opening at the distal tip of the needle, perhaps impeding a surgeon's ability to infuse all desired areas and/or requiring an additional procedural step of "backing" the needle tip away from the desired delivery site. Also, because the needle tip, and thus the axial opening, is likely at or facing the bone defect (e.g., fracture in the vertebral body) being repaired, the stabilizing material may be injected directly at the defect, giving rise to a distinct possibility that the stabilizing material will forcibly progress through and outwardly from the defect. This is clearly undesirable. The issues and concerns described above in the context of percutaneous vertebroplasty can also arise in similar surgical procedures at other bone sites.

The injection of palliative materials into damaged or compromised bone sites has proven highly beneficial for patients. However, the known access and infusion techniques necessitate multiple needle sticks and/or risk coring bone or tissue. Therefore, a need exists for an improved device and system for delivering stabilizing material to damaged or compromised bone sites. Another technique has been developed wherein a cavity or void within a bone (e.g., in cancellous bone) may be created using a needle to provide for enhanced introduction of palliative materials. A need exists to provide for controlled manipulation of the needle during this technique.

BRIEF SUMMARY

Benefits achieved in accordance with principles of the disclosed invention include a delivery cannula providing a non-traumatic, blunt distal end that minimizes the risks of coring tissue or puncturing bone or tissue during intraosseous procedures without requiring additional components (such as separate wire). Other benefits relate to a delivery cannula defining at least one side orifice adjacent to a blunt distal end, where the orifice(s) permit a radial infusion of a curable material at a site within bone even in the case where the distal end is in contact with bone and/or tissue. Thus, a palliative bone procedure can be accomplished with reduced operating room time and with fewer approaches of surgical instruments to the bone site. For example, unipedicular vertebroplasty is readily accomplished. Further, virtually any area within the surgical site can be accessed. Also, the distal end of the delivery cannula can be placed as close as desired to a particular anatomical feature of the surgical site (e.g., a bone fracture) without fear that subsequently delivered material will forcibly progress into or through that feature.

Other benefits achieved in accordance with principles of the disclosed invention include a curved needle with sufficient strength to allow it to be used for creating a void in cancellous bone tissue to enhance introduction of a palliative material (e.g., curable bone cement material). Other benefits include one or more spacers that may be used to control the size and location of a void being created by controlling the depth and exposed curvature of a needle within, for example, a vertebral body.

Some aspects of the present invention relate to a delivery cannula device for delivering a curable material into bone. The device includes a delivery cannula and a hub forming a fluid port. The delivery cannula defines a proximal end, a deflectable segment, a distal end, a lumen, and at least one side orifice. The proximal end is axially open to the lumen. The deflectable segment is formed opposite the proximal end and terminates at the distal end that is otherwise axially closed. Further, the distal end has a blunt tip. The lumen extends from the proximal end and is fluidly connected to the side orifice(s). To this end, the side orifice(s) is formed adjacent to, and proximally space from, the distal end. Finally, the deflectable segment forms a curved shape in longitudinal extension and has a shape memory characteristic. With this configuration, the deflectable segment can be forced to a substantially straightened shape and will revert to the curved shape upon removal of the force. The hub is fluidly coupled to the proximal end of the delivery catheter. With this construction and during use, the distal end will not damage or core tissue when inserted into a delivery site within bone due to the blunt tip. Further, the side orifice(s) afford the ability to inject a curable material regardless of whether the distal end is lodged against bodily material, and can achieve more thorough dispensing.

Other aspects of the present invention relate to an intraosseous, curable material delivery system for delivering a curable material, such as bone cement, to a delivery site within bone. The system includes the delivery cannula and hub as described in the previous paragraph, along with a guide cannula. The delivery cannula and the guide cannula are sized such that the delivery cannula is slidable within the guide cannula. To this end, the deflectable segment is configured to deflect to a substantially straightened shape when inserted within the cannula and revert to the curved shape when extended distal the guide cannula for delivery of the curable material. In one embodiment, the guide cannula and the delivery cannula are sized to perform a vertebroplasty procedure. The system may further include one or more spacers that may be engageable with one or both of the delivery cannula and the guide cannula and that may be configured to provide control of both the depth of introduction of the deflectable segment and—thereby—the depth and the diameter of a void that may be created in the event that the deflectable segment is rotated relative to the guide cannula.

Yet other aspects of the present invention relate to a method of stabilizing a bone structure of a human patient. The method includes providing a delivery cannula as previously described. A distal tip of a guide cannula is located within the bone structure. The delivery cannula is inserted within the guide cannula. In this regard, the deflectable segment deflects to a substantially straightened shape within the guide cannula. The delivery cannula is distally advanced relative to the guide cannula such that the distal end and at least a portion of the deflectable segment of the delivery cannula projects distal the distal tip of the guide cannula. To this end, the portion of the deflectable segment distal the distal tip of the guide cannula naturally reverts to the curved shape. The distal end of the delivery cannula is positioned adjacent a desired delivery site within the bone structure. A curable material is injected into the lumen. The injected curable material is delivered to the delivery site via the side orifice(s). Once delivered, the curable material is allowed to cure so as to stabilize the bone structure. In one embodiment, the method further includes rotating the delivery cannula relative to the guide cannula so as to alter a spatial position of the side orifice(s), thus affording the ability to inject the curable material in different planes.

Still another aspect of the present invention relates to a method of injecting curable material to a delivery site within a bone structure. The method includes the steps of providing a delivery cannula having an open, proximal end, a deflectable segment opposite the proximal end having a distal end, and a lumen extending from the proximal end. The deflectable segment has a shape memory characteristic and naturally assumes a curved shape in longitudinal extension. The method also includes the step of locating a distal tip of a guide cannula within the bone structure. The method further includes the step of inserting the delivery cannula within the guide cannula, wherein the deflectable segment deflects to a substantially straightened shape within the guide cannula, and distally advancing the delivery cannula such that the distal end and at least a portion of the deflectable segment projects distal the distal tip. The portion of the deflectable segment distal the distal tip then naturally reverts to the curved shape. The method also includes the step of manipulating the delivery cannula such that at least a portion of the deflectable segment creates one or more voids in soft body tissue within the bone structure. The size(s) of the void(s) may be controlled by engaging one or more spacers near a proximal portion of the delivery cannula, where the spacers are configured to control a relative longitudinal position of the delivery cannula and the guide cannula. The spacers may also control an effective exposed curvature of the delivery cannula, which can control the diameter, as well as the depth, of the void(s). The method also includes the step of delivering the curable material to the delivery site wherein the curable material is delivered to the one or more voids in the soft body tissue created by the deflectable segment.

Yet another aspect of the present invention relates to a method of injecting curable material to a delivery site within a bone structure. The method includes the step of providing a delivery cannula having an open, proximal end, a deflectable segment opposite the proximal end having a distal end and a lumen extending from the proximal end. The deflectable segment has a shape memory characteristic and naturally assumes a curved shape in longitudinal extension. In the method, the distal tip of a guide cannula is located within the bone structure. The delivery cannula is inserted within the guide cannula, characterized by the deflectable segment deflecting to a substantially straightened shape within the guide cannula. The delivery cannula is distally advanced such that the distal end and at least a portion of the deflectable segment projects distal the distal tip, characterized by the portion of the deflectable segment distal the distal tip naturally reverting to the curved shape. The distal end is positioned distally adjacent a first region within the delivery site. The curable material is then delivered to the first region within the delivery site. The distal end is then positioned adjacent a second region within the delivery site and curable material is delivered to the second region within the delivery site. Using one or more spacers may provide positional control and accuracy of delivery to a plurality of desired regions within a delivery site.

Yet another aspect of the present invention relates to a cannula device for delivering a curable material, such as bone cement, into bone as part of a curable material delivery system. The device includes a delivery cannula preloaded with bone cement defining an open, proximal end, a deflectable segment opposite the proximal end and terminating in a closed distal end. The device also includes a lumen extending from the proximal end. The device also includes at least one side orifice formed adjacent to, and proximally spaced from, the distal end and fluidly connected to the lumen, wherein the deflectable segment forms a curved shape in longitudinal extension and has a shape memory characteristic such that the deflectable segment is configured to assume a longitudinally, substantially straightened form when subjected to a force and naturally revert to the curved shape upon removal of the force.

Yet another aspect of the present invention relates to an intraosseous, curable material delivery system for delivering a curable material such as bone cement to a delivery site within bone. The system includes a delivery cannula having an open, proximal end, a deflectable segment opposite the proximal end and terminating in a distal end, a lumen extending from the proximal end, wherein the deflectable segment has a shape memory characteristic and assumes a curved shape in longitudinal extension. The system also includes a guide cannula defining an inner diameter greater than an outside diameter of the delivery cannula and having an open distal tip wherein the deflectable segment is configured to be deflectable to a substantially straightened shape such that the delivery cannula is slidable within the guide cannula, and to naturally revert to the curved shape when extended distal the distal tip for delivery of a curable material within implantation site via the distal end and wherein the delivery cannula is smoothly slidable within the guide cannula.

Yet another aspect of the present invention relates to a curable material structure for stabilizing a vertebral body. The structure includes a first curable material deposit proximal to an endplate of a vertebral body for providing support to a first endplate of the vertebral body. The structure also includes a second curable material deposit proximal to an endplate of a vertebral body for providing support to a second endplate of the vertebral body. The structure also includes a column of curable material between the first curable material deposit and the second curable material deposit for providing support to the vertebral body.

BRIEF DESCRIPTION OF THE DRAWINGS

The accompanying drawings are included to provide a further understanding of the present invention and are incorporated in and are a part of this specification. Other embodiments of the present invention, and many of the intended advantages of the present invention, will be readily appreciated as they become better understood by reference to the following detailed description. The elements of the drawings are not necessarily to scale relative to each other. Like reference numerals generally designate corresponding similar parts.

FIG. 6B is a cross-sectional view of a portion of the system of FIG. 6A;

FIGS. 10A-10C are simplified lateral views of a vertebral body, illustrating use of the system in stages with spacer elements implemented for creating voids;

DETAILED DESCRIPTION

Figure 1:
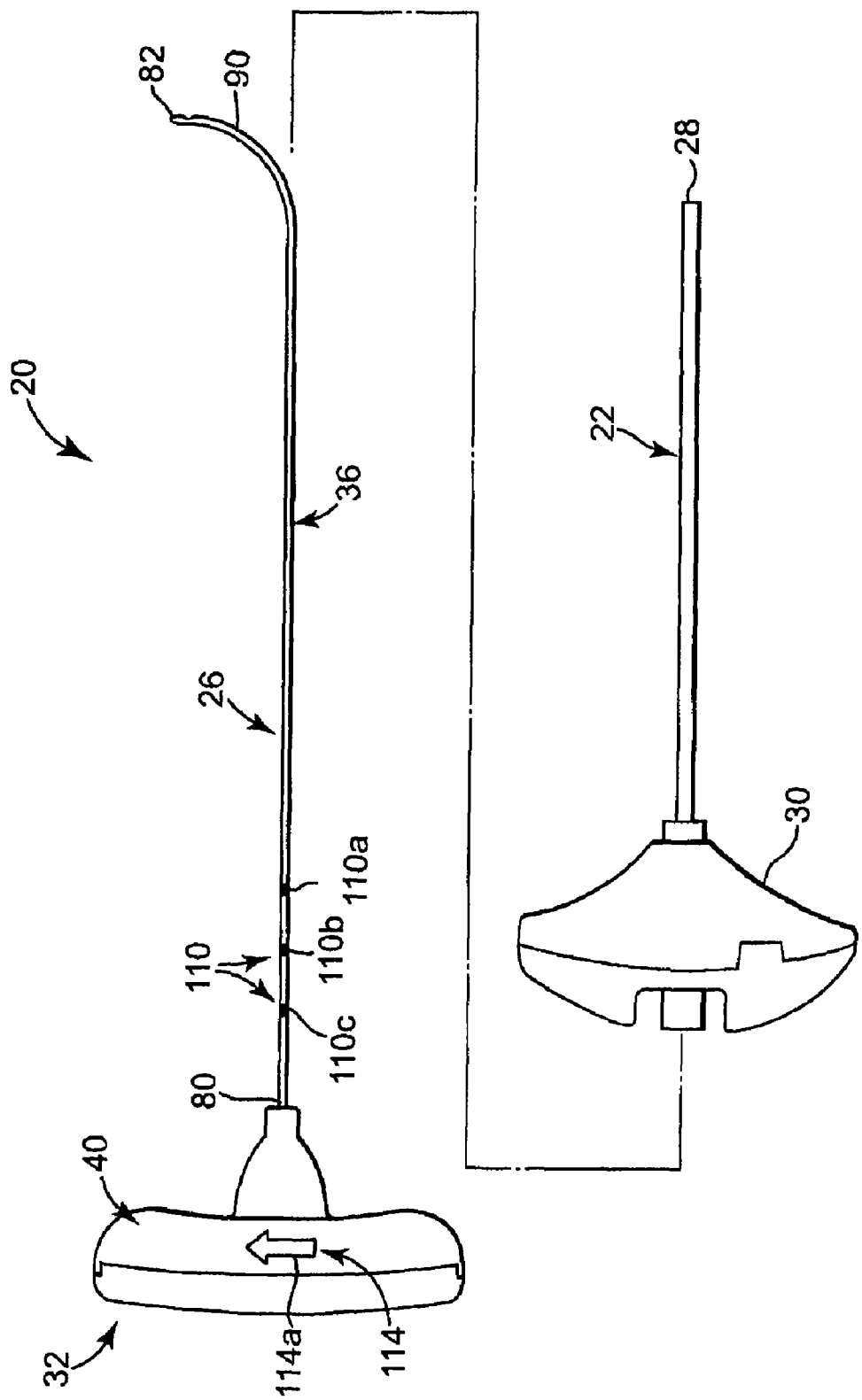
FIG. 1 illustrates components of an intraosseous curable material delivery system in accordance with principles of the present invention.

FIG. 1 illustrates components of one embodiment of an intraosseous, curable material delivery system 20. The system 20 includes an outer guide cannula 22 and a delivery cannula device 26 (referenced generally). Details on the various components are provided below. In general terms, however, a portion of the delivery cannula device 26 is sized to be slidably disposed within the guide cannula 22 that otherwise serves to form and/or locate a desired delivery site within bone. Once positioned, the delivery cannula device 26 is employed to inject a curable, bone stabilizing material into the delivery site. The system 20 can be used for a number of different procedures, including, for example, vertebroplasty and other bone augmentation procedures in which curable material is delivered to a site within bone, as well as to remove or aspirate material from a site within bone.

The system 20, and in particular the delivery cannula device 26, is highly useful for delivering a curable material in the form of a bone cement material. The phrase "curable material" within the context of the substance that can be delivered by the system/device of the invention described herein is intended to refer to materials (e.g., composites, polymers, and the like) that have a fluid or flowable state or phase and a hardened, solid or cured state or phase. Curable materials include, but are not limited to injectable polymethylmethacrylate (PMMA) bone cement, which has a flowable state wherein it can be delivered (e.g., injected) by a cannula to a site and subsequently cures into hardened cement. Other materials, such as calcium phosphates, bone in-growth material, antibiotics, proteins, etc., could be used in place of or to augment, PMMA (but do not affect an overriding characteristic of the resultant formulation having a flowable state and a hardened, solid or cured state). This would allow the body to reabsorb the cement or improve the clinical outcome based on the type of filler implant material. With this in mind, and in one embodiment, the system 20 further includes a source (not shown) of curable material fluidly coupled to the delivery cannula device 26.

Given the above, the outer guide cannula 22 generally enables access of the delivery cannula device 26 to a bone site of interest, and thus can assume a wide variety of forms. In general terms, however, the guide cannula 22 is sized to slidably receive a portion of the delivery cannula device 26, terminating in an open, distal tip 28. The distal tip 28 can further be adapted to facilitate coring of bone tissue, such as when using the guide cannula 22 to form a delivery site within bone. To promote a desired interface between the guide cannula 22 and a portion of the delivery cannula device 26 otherwise slidably inserted within the guide cannula 22 during use (described below), in one embodiment, an inner diameter surface of the guide cannula 22 is highly smoothed to a matte or mirror finish (i.e., RMS range of about 0-16). In another preferred embodiment, the inner diameter surface of the guide cannula 22 or the outer diameter surface of the delivery cannula 36 can be coated with Teflon to promote a smooth desired interface between the guide cannula 22 and a portion of the delivery cannula device 26 otherwise slidably inserted within the guide cannula 22 during use. A Teflon sleeve between the guide cannula 22 and a portion of the delivery cannula device 26 may also be used. Further, the outer diameter surface of the delivery cannula 36 can be polished to a highly smoothed to a matte or mirror finish (i.e., RMS range of about 0-16). Regardless, and in some embodiments, the guide cannula 22 can further be attached, at a proximal end thereof, to a handle 30 for enhancing a surgeon's ability to manipulate the system 20. Alternatively, the handle 30 can be eliminated.

Figure 1A:
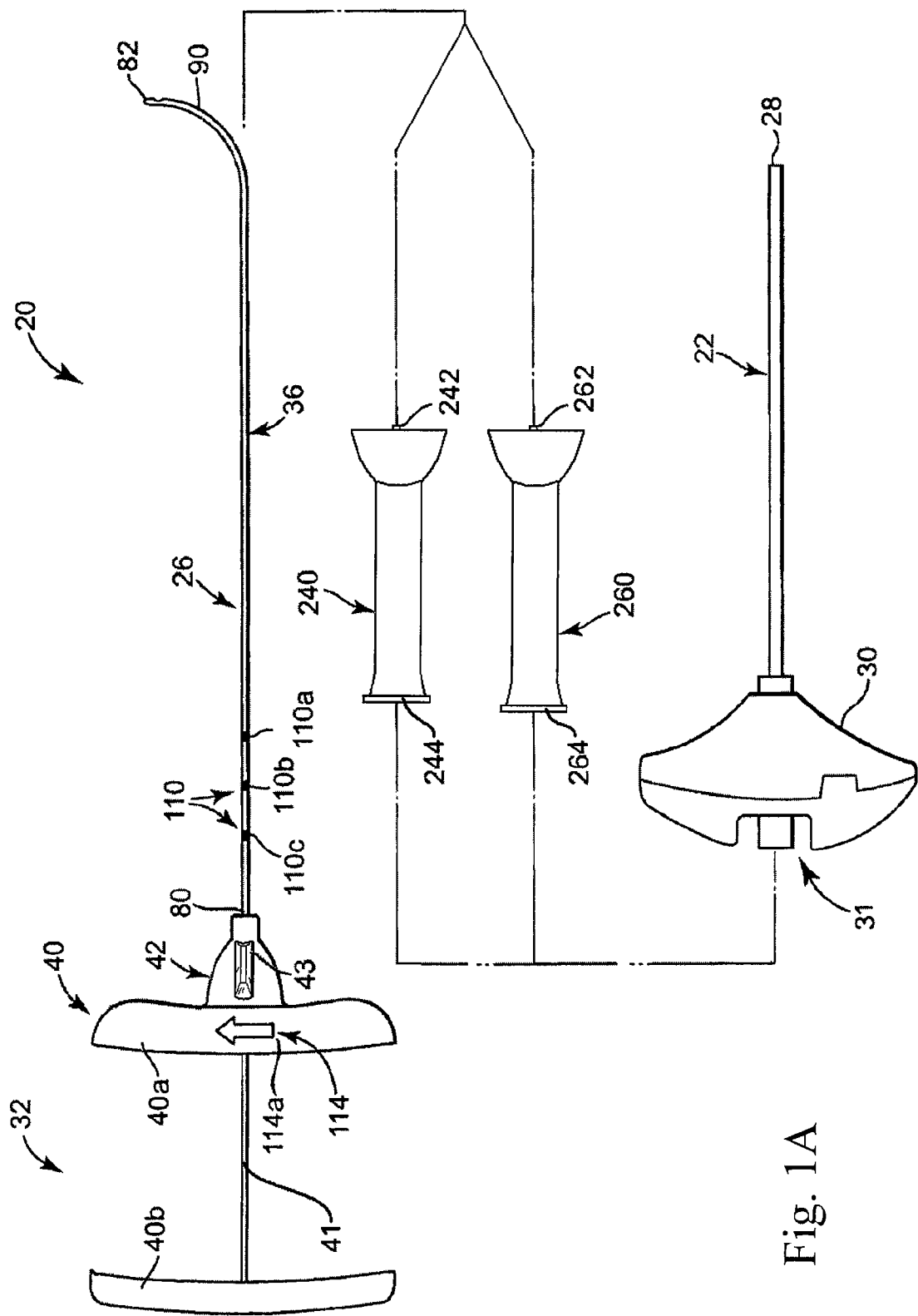
FIG. 1A shows the system components of FIG. 1 modified for and including spacer elements.

FIG. 1A shows an alternative embodiment of the system 20 of FIG. 1. It includes two spacer elements 240, 260, each of which is configured to be disposed onto the delivery cannula 36 of the delivery cannula device 26 between its handle 40 and the guide cannula handle 30. At least one spacer element may be included in the system 20 for controlling the relative position of the delivery cannula device 26 and the guide cannula device 22. In preferred embodiments, one or more spacers will be provided and configured to control that relative position in a manner that controls the depth of penetration by distal delivery cannula end 82 and/or the sweep allowed by the curve 90 of the delivery cannula 36 if/when it is rotated about the longitudinal axis of the delivery cannula device 26. The spacers 240, 260 and their use are described below in greater detail with reference to FIGS. 10-10C, 13A-13B, and 14.

In the embodiment shown in FIG. 1A, the retainer 42 includes external detent grooves 43 configured to engage detent ribs 242, 262 of the spacers 240, 260. As is described below, the grooves 43 are configured to longitudinally receive the detent ribs of the spacers, but to prevent the spacers from rotating about the common longitudinal axis of the spacers and the cannula device 26. In certain embodiments one or both of the ribs and grooves may also include one or more raised nubs and/or indentations configured to retain a spacer in an easily-removable configuration relative to the retainer 42.

The embodiment shown in FIG. 1A includes two portions of the handle 40: a distal handle portion 40a and a proximal handle portion 40b. The proximal handle portion 40b includes an obturator 41 that, when present, will extend through the lumen of the delivery cannula 36. The distal base portion 244, 264 of each spacer is configured to engage the proximal indentation and nub 31 of the guide cannula handle 30 in a manner allowing the handle 40 to rotate freely about its longitudinal axis when the spacer is engaged with the guide cannula handle 30. As will be appreciated with reference to FIG. 1A, the shorter spacer 240 will allow the delivery cannula 36 to extend further beyond the distal end of the guide cannula 30 than will the longer spacer 260. Depending upon the relative lengths of the guide cannula 30 and the delivery cannula 36, it will also be appreciated that the presence of a spacer may also affect the exposed distal curve 90 of the delivery cannula (i.e., a sufficiently long spacer will allow less than the entire curve 90 to be exposed, thereby providing a smaller sweep radius of the distal delivery cannula end when it is rotated about its longitudinal axis).

Figure 2A:
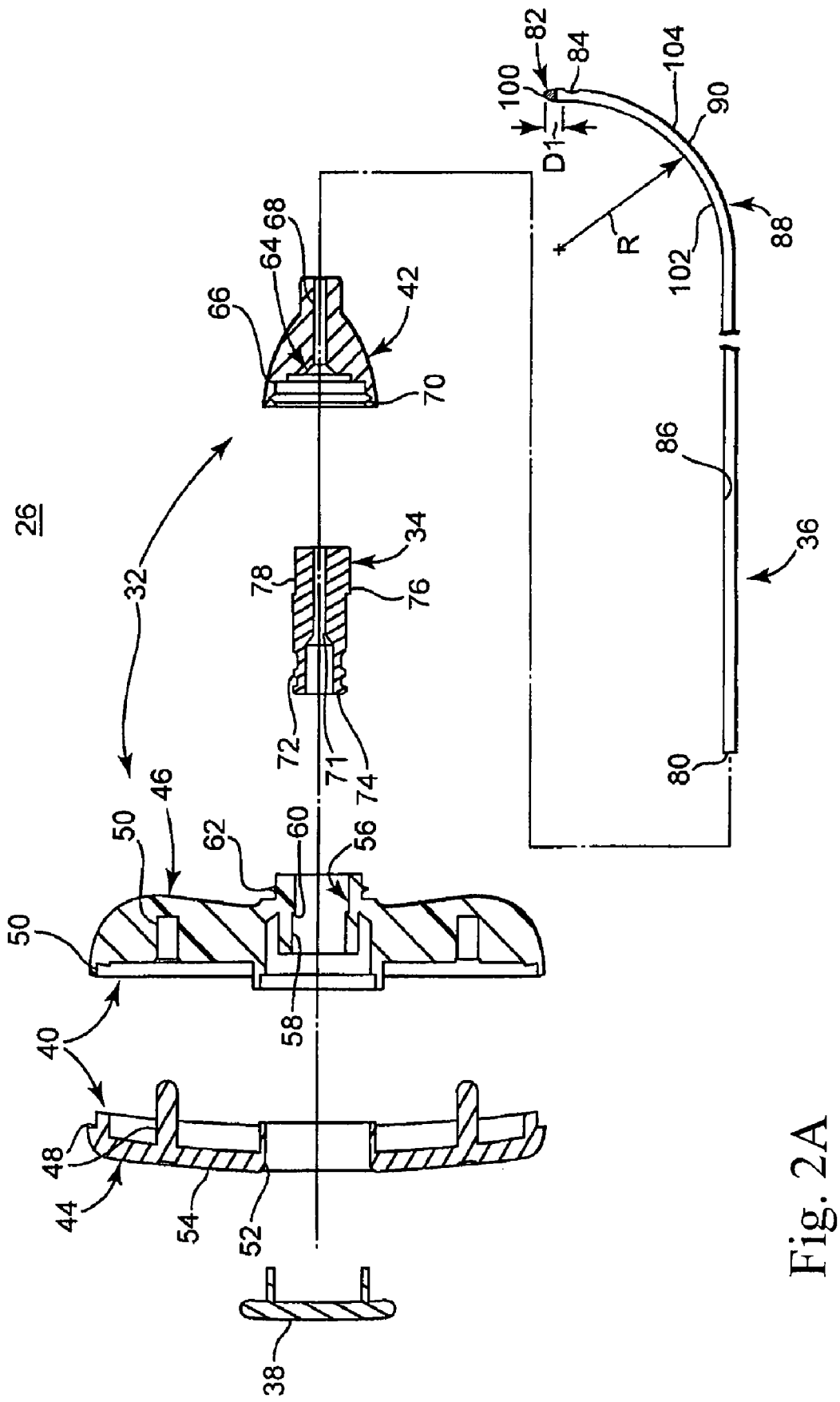
FIG. 2A is a cross-sectional, exploded view of a delivery cannula device component of the system of FIG. 1.

The delivery cannula device 26 is shown in greater detail in FIG. 2A, and generally includes a handle assembly 32 (referenced generally), a hub 34, and a delivery cannula 36. The hub port 34 forms a fluid port and is fluidly connected to the delivery cannula 36, with the handle assembly 32 retaining the combination hub 34/delivery cannula 36. As described in greater detail below, the delivery cannula 36 is sized to be coaxially, slidably received within the guide cannula 22 (FIG. 1), and is adapted to deliver a curable material injected therein via the hub 34.

The handle assembly 32 includes, in one embodiment, a handle 40 and a retainer 42. The handle 40 is adapted to receive the hub 34, with the retainer 42 securing the hub 34 (and thus the delivery cannula 36) to the handle 40.

The handle 40 (or, for the embodiment of FIG. 1A, the distal handle portion 40a), may include a first section 44 and a second section 46. The first section 44 may be configured for snap-fit assembly with the second section 46, such as by complimentary annular protrusion(s) 48 and grooves 50. The first section 44 forms a central passage 52 extending inwardly from an exterior surface 54 thereof. In this embodiment, the second section 46 defines an internal aperture 56 that, upon final assembly of the handle 40, is aligned with the central passage 52. The aperture 56 may assume a variety of forms sized to receive the hub 34 in a nested manner. The nested interface between the handle 40 and the hub 34 is preferably adapted such that the hub 34 cannot rotate relative to the handle 40 upon final assembly (i.e., the hub 34/handle 40 interface resists a torque imparted on either component such that rotational movement of the handle 40 results in an identical rotation of the hub 34/delivery cannula 36 even when the delivery cannula 36 is inserted within a confined surgical site). Thus, in one embodiment, the aperture 56 and the hub 34 (as described below) may have corresponding non-symmetrical or non-circular shapes in transverse cross-section. Relative to the longitudinal cross-sectional view of FIG. 2A, the non-circular shape of the aperture 56 is characterized by the aperture 56 being defined by a sidewall 58 having a shoulder 60 corresponding with the shape of the hub 34 as described in greater detail below. Alternatively, the sidewall 58 can assume a variety of other configurations. In one embodiment, the second section 46 forms exterior threads 62.

The retainer 42 is configured to secure the hub 34 with delivery cannula 36 to the handle 40, and forms a central opening 64 defining a proximal portion 66 and a distal portion 68. The proximal portion 66 forms the central opening 64 to have a diameter slightly greater than that of the hub 34, along with internal threads 70 sized to threadably engage the exterior threads 62 of the handle 40. The distal portion 68 forms the opening 64 to have a diameter approximating an outer diameter of the delivery cannula 36 so as to provide a more rigid connection between the handle assembly 32 and the hub 34/delivery cannula 36. Alternatively, the handle assembly 32 can assume a wide variety of other forms and in some embodiments can be eliminated entirely.

Figure 2B:
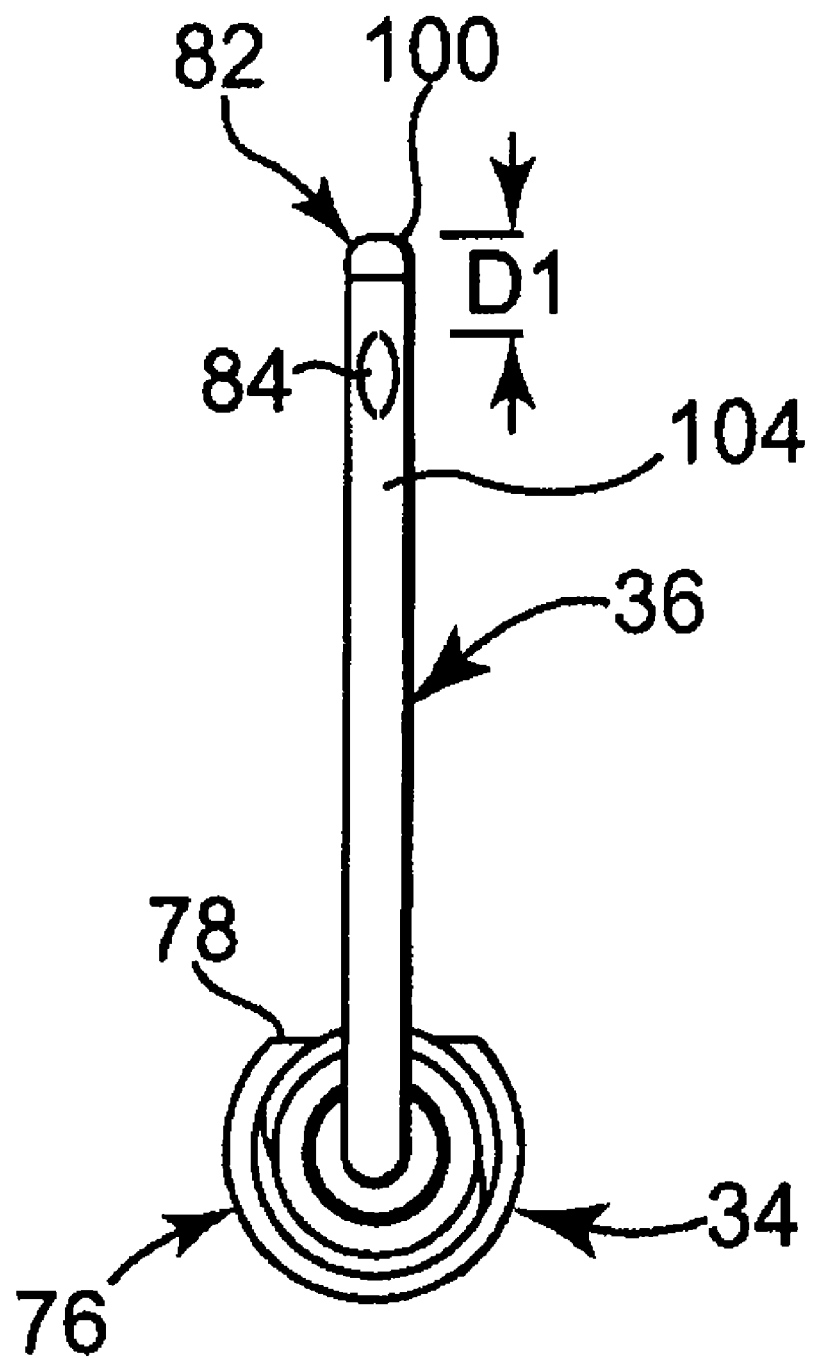
FIG. 2B is a front view of a delivery cannula and hub portions of the device of FIG. 2A.

In one embodiment, the hub 34 is of a conventional fluid port design and defines a fluid passage 71 and an exterior thread 72 on a proximal end 74 thereof. In one embodiment, the thread 72 is a double start right hand Luer thread including a 5-millimeter lead, although other thread conformations and lead sizes are also acceptable. Regardless, as previously mentioned, in one embodiment, the hub 34 is configured to be rotatably "locked" relative to the handle assembly 32 upon final assembly. Thus, in one embodiment, a body of the hub 34 forms a generally cylindrical surface 76 a portion of which is flattened in an area 78, as shown in FIG. 2B. The size and shape of the flattened area 78 corresponds with the aperture sidewall 58 (FIG. 2A) provided with the handle 40 (FIG. 2A).

The hub 34 is formed, in one embodiment, of a sterilizable polymeric material. By way of example, the hub 34 can be formed of a polylac 717C acrylonitrile-butadiene-styrene (ABS) copolymer, although other sterilizable polymers and/or copolymers are also acceptable.

In another preferred embodiment, a removable cap 38 is adapted to attach to the first section 44 of the handle assembly 32 and cover the fluid passage 71 of the hub 34. When the delivery cannula 36 is inserted into the guide cannula, 22, blood or other fluids may travel within the delivery cannula 36 and exit through the fluid passage 71 of the hub 34. A removable cap 38 can be attached to the handle assembly 32 as the delivery cannula 36 is introduced into the guide cannula 22. After inserting the delivery cannula 36 to the desired location, the removable cap 38 is removed to allow access to the hub 34.

Returning to FIG. 2A, the delivery cannula 36 defines a proximal end 80 and a distal end 82, and forms one or more side orifices 84 adjacent the distal end 80 and in fluid communication with an internal lumen 86. In addition, the delivery cannula 36 includes a deflectable segment 88 (referenced generally) defining a pre-set curve or bend 90. As described below, the deflectable segment 88, and in particular the bend 90, includes or extends from the distal end 82, and has a shape memory attribute whereby the deflectable segment 88 can be forced from the curved shape (shown in FIG. 2A) to a substantially straightened shape, and will naturally revert back to the curved shape upon removal of the force.

The proximal end 80 is axially open to the lumen 86. Conversely, the distal end 82 is axially closed to the lumen 86 (i.e., material cannot be axially expelled from the distal end 82 relative to an axis of the lumen 86). That is to say, material in the lumen 86 cannot be forced distally therefrom in an axial fashion. Further, the distal end 82 defines or includes a blunt tip 100. For example, in one embodiment, the blunt tip 100 defines a hemispherical surface, although other blunt (i.e., curved or curvilinear) shapes or contours are also acceptable. The blunt tip surface 100 is adapted to provide a non-traumatic surface suitable for accessing, contacting and probing bone or tissue while minimizing the risk of puncture and/or coring of the tissue or damage to the bone. To enhance a desired softness, the blunt tip 100 can have a differing thickness as compared to a remainder of the delivery cannula 36 such as by sintering the distal end 82 to form the blunt tip 100 (when the delivery cannula 36 is initially provided as a continuous tube). Alternatively, the blunt tip 100 can be formed apart from a remainder of the delivery cannula 36 and subsequently attached to the delivery cannula 36 to form the distal end 82 (e.g., the delivery cannula 36 can include a first tubular body formed of a hardened material along with a second, solid body formed of a softer material attached (e.g., welded) to the tubular body to form the distal end 82/blunt tip 100).

With reference to FIGS. 2A and 2B, the side orifice(s) 84 is formed adjacent the distal end 82, extending through a thickness of a sidewall of the delivery cannula 36. In one embodiment, a single orifice 84 is provided, and is located "opposite" a direction of the bend 90. In other words, relative to the longitudinal cross-sectional view of FIG. 2A, a direction of the bend 90 serves to form the delivery cannula 36 to define an interior bend side 102 and an exterior bend side 104. With these designations in mind, the side orifice 84 is formed along, and is open relative to, the exterior bend side 104. It has surprisingly been found that by positioning the side orifice 84 "opposite" the bend 90, users will experience enhanced control over the direction in which curable material is distributed from the delivery cannula 36, as well as improved safety. Alternatively, a greater number of side orifices 84 can be provided that may or may not be circumferentially aligned and may or may not be located along the exterior bend side 104 of the delivery cannula 36. In general, the side orifice 84 is offset at least a distance D1 from the distal end 82. In one embodiment, the distance D1 is between 0.05 inches and 0.5 inches, and preferably the distance D1 is between 0.1 inches and 0.25 inches. With this configuration, even when the blunt tip 100 is pressed against tissue or bone, the side orifice(s) 84 is "open" and thus available for dispensing (or aspirating)

material. Further, the side orifice(s) 84 provides a radial dispensing or flow direction relative to a longitudinal axis of the delivery cannula 36.

The side orifice(s) 84 can assume a wide variety of shapes and sizes (relative to an exterior surface of the delivery cannula 36). For example, the side orifice(s) 84 can be oval, circular, curvilinear, etc. In one embodiment, and with reference to FIG. 3A, a chamfered region 106 can be formed about the side orifice 84 to eliminate sharp edges along an exterior of the delivery catheter 36 as well as to promote consistent flow of curable material from the side orifice 84 (via the expanding orifice size effectuated by the chamfered region 106). With embodiments where the side orifice 84 is non-circular, an orifice length L and width W are defined. To this end, the length L is greater than 0.050 inch, preferably greater than 0.075 inch, and even more preferably greater than 0.100 inch. While the width W of the side orifice 84 may or may not be less than the length L (e.g., on the order of 0.042 inch in one embodiment), the side orifice 84 is properly characterized as being relatively large, especially as compared to conventional bone cement delivery needles that otherwise provide only an axial orifice or opening at the distal tip.

Figure 3A:
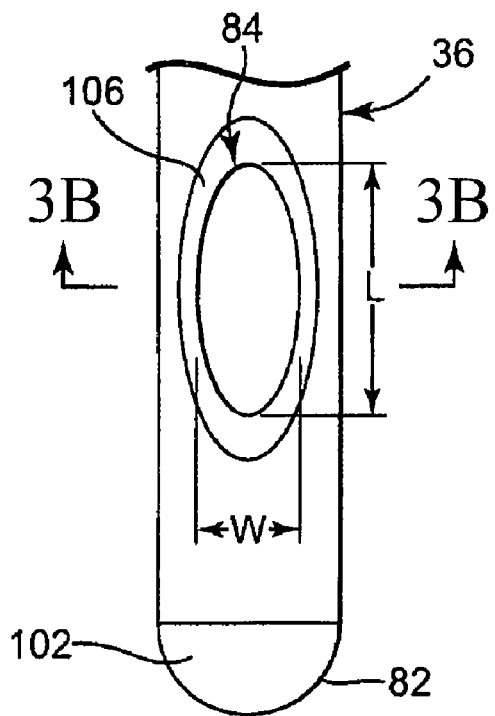
FIG. 3A is an enlarged plan view of a distal portion of the delivery cannula of FIG. 2A.
Figure 3B:
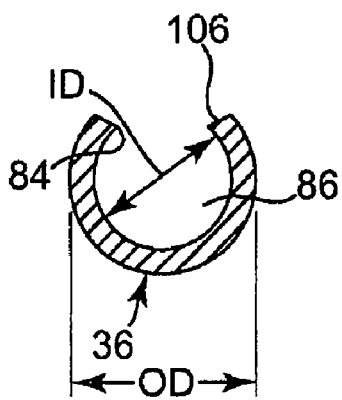
FIG. 3B is a cross-sectional view of the delivery cannula of FIG. 3A.

In particular, and with additional reference to FIG. 3B (otherwise illustrating a cross-sectional view of the delivery cannula 36 taken through the side orifice 84), the delivery cannula 36 defines an inside diameter ID (i.e., a diameter of the lumen 86). The side orifice 84 is fluidly connected to the lumen 86 and extends in a radial fashion. With these conventions in mind, in one embodiment, the length L of the side orifice 84 is greater the inside diameter ID of the delivery cannula 36. As such, at least one linear dimension of the side orifice 84 is larger than any orifice dimension that could otherwise be achieved were an orifice to be formed at the distal end 82 (i.e., an axially extending orifice). That is to say, an orifice formed at the distal end 82 of the delivery cannula 82 (as is conventionally employed in the bone cement delivery needle art) is limited in size (i.e., diameter) by the inside diameter ID of the delivery cannula 36. In contrast, the side orifice 84 in accordance with principles of the present invention is much larger, presenting a distinct advantage when attempting to pass a low viscosity liquid (curable material such as bone cement) there through.

Figure 3E:
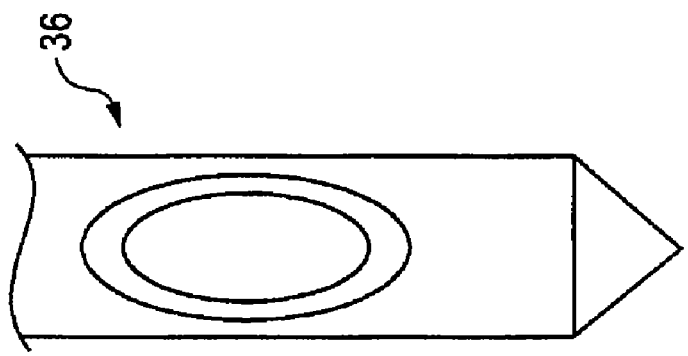
FIG. 3E is an enlarged plan view of a distal portion of the delivery cannula of FIG. 2A according to another preferred embodiment of the present invention.
Figure 3D:
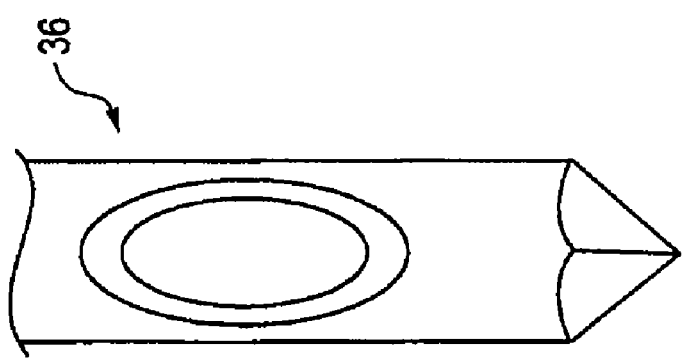
FIG. 3D is an enlarged plan view of a distal portion of the delivery cannula of FIG. 2A according to another preferred embodiment of the present invention.
Figure 3C:
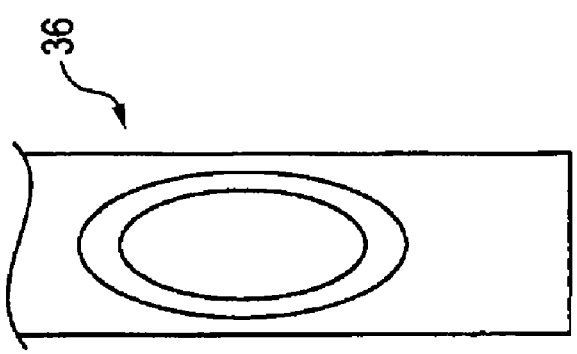
FIG. 3C is an enlarged plan view of a distal portion of the delivery cannula of FIG. 2A according to another preferred embodiment of the present invention.

With reference to FIGS. 3C-3E, the closed distal end 82 of the delivery cannula 36 can embody numerous different configurations in addition to the rounded distal end 82 depicted in FIG. 3A. The closed distal end 82 may also be a substantially flat tip, as depicted in FIG. 3C, a sharp "trocar" tip, as depicted in FIG. 3D, or a sharp "pencil" tip, as depicted in FIG. 3E. The flat tip advantageously reduces the risk of puncture though body tissue. Conversely, when desired, the sharp tip configurations advantageously allow a physician to push the delivery cannula 36 through body tissue with less force than with a blunt tip.

Returning to FIG. 2A, in one embodiment, the delivery cannula 36 defines a continuous length between the proximal end 80 and the distal end 82, with the deflectable segment 88, and in particular the bend 90, extending along approximately 25% of the length from the distal end 82 (where the "length" of the delivery cannula 36 is the length of extension from the hub 34 upon final assembly). In other embodiments suited for other surgical procedures, the deflectable segment 88, and in particular the bend 90, extends along between 10%-50% of the length of the delivery cannula 36 as measured from the distal end 82.

To facilitate delivery of a curable material (e.g., bone cement) into a confined site within bone (such as with a vertebroplasty procedure), the deflectable segment 88 can be formed to define the bend 90 at a pre-determined radius of curvature R appropriate for the procedure in question. In one embodiment, the bend 90 is J-shaped (approximating at least a 90 degree bend) and defines the radius of curvature R to be less than 1.5 inches, preferably in the range of 0.25-1.5 inches. In one preferred embodiment, the bend 90 defines the radius of curvature R to be approximately 1 inch. Alternatively, and as described in greater detail below, the radius of curvature R can be greater or lesser, depending upon the particular procedure for which the delivery cannula 36 is to be employed.

Further, to facilitate ready deflection of the deflectable segment 88 from the curved shape to a substantially straightened state (such as when the delivery cannula 36 is inserted within the outer guide cannula 22 (FIG. 1)) and reversion back to the curved shape, the delivery cannula 36, or at least the deflectable segment 88, is formed of a shape memory metal. In one embodiment, the delivery cannula 36 comprises Nitinol™, a known shape memory alloy of nickel (Ni) and titanium (Ti). In one embodiment, the bend 90 is formed in the delivery cannula 36 by deforming a straight fluid delivery cannula under extreme heat for a prescribed period of time, which pre-sets a curved shape in the delivery cannula 36.

In another embodiment, the pre-set curve or bend 90 is formed in an initially straight cannula by cold working the straight cannula and applying a mechanical stress. Cold working permanently locks a crystalline structure (for example, a partial martensitic crystalline structure) in a portion (i.e., the deflectable segment 88) of the cannula, while an unstressed portion remains in, for example, an austenitic structure.

In addition to Nitinol, other materials exhibiting this shape memory behavior can be employed, including superelastic or pseudoelastic copper alloys, such as alloys of copper, aluminum, and nickel, and alloys of copper, aluminum, and zinc, and alloys of copper and zinc. Regardless, the deflectable segment 88 is formed to be resilient and to naturally assume the desired radius of curvature R. In this manner, after the delivery cannula 36, and in particular the deflectable segment 88, is flexed to a substantially straightened shape (not shown), upon a subsequent relaxation, the deflectable segment 88 "remembers" the pre-set curved shape and reversibly relaxes/returns to the bend 90, as described in detail below.

The above material selection in combination with delivery of curable liquid through one or more, relatively large side orifice(s) (otherwise positioned proximal of the distal end 82) and the blunt tip 100 has surprisingly been found to allow the delivery cannula 36 to be smaller and thinner than conventional bone cement delivery needles (i.e., having an outer diameter of approximately 0.125 inch, yet still provide sufficient structural integrity to perform all desired procedures entailing delivery of curable material to, or removal of material from, a site within bone. More particularly, and as best shown in FIG. 3B, the delivery cannula 36 defines the inside diameter (ID) and an outside diameter (OD). In one embodiment, the inside diameter ID is in the range of 0.040-0.090 inch, preferably in the range of 0.050-0.080 inch, and more preferably in the range of 0.047-0.067 inch. The outside diameter OD is selected to permit the delivery cannula 36 to be co-axially received by the outer guide cannula 22 (FIG. 1). With this in mind, and in one embodiment, the outside diameter OD is in the range of 0.030-0.10 inch, preferably not greater than 0.090 inch, more preferably in the range of 0.060-0.090 inch, and more preferably in the range of 0.072-0.082 inch. Thus, in one embodiment, the delivery cannula 36 is of a reduced outer diameter and thickness as compared to available bone cement delivery needles (e.g., the curved needle available with some existing product lines has an outside diameter of 0.092 inch and a wall thickness of 0.027 inch). By way of example, but in no way limiting, an exemplary delivery catheter was constructed in accordance with principles of the present invention having an outside diameter of approximately 0.077 inch and a wall thickness of 0.015 inch, and was found to be highly suitable for performing a vertebroplasty procedure. This represents a distinct advancement not heretofore available to surgeons.

An additional feature of the delivery cannula 36 in accordance with one embodiment is best shown in the plan view of FIG. 1. More particularly, the delivery cannula 36 includes indicia 110 (reference generally) adjacent the proximal end 80. The indicia 110 is indicative of a location of the distal end 82 relative to the distal tip 28 of the guide cannula 22 upon insertion of the delivery cannula 36 within the guide cannula 22. For example, the indicia 110 can include first, second, and third depth markings 110a, 110b, 110c. A longitudinal location of the first depth marking 110a relative to the distal end 82 (when the delivery cannula 36 is forced to a substantially straightened state) is commensurate with a length of the guide cannula 22 in combination with the handle 30 (where provided). That is to say, the first depth marking 110a is located at a linear distance from the distal end 82 such that upon insertion of the delivery cannula 36 within the guide cannula 22 (otherwise forcing the delivery cannula 36 to a substantially straightened state), when the distal end 82 is at or even with the distal tip 28 of the guide cannula 22, the first depth marking 110a will be proximally adjacent or aligned with (and visible relative to) a proximal side of the handle 30. Thus, a user can quickly and easily have visual confirmation that the distal end 82 is within the guide cannula 22. The second and third depth markings 110b, 110c are proximally spaced from the first depth marking 110a at known increments (e.g., 0.5 cm, 1.0 cm, etc.) that represent length of distal extension of the distal end 82 relative to the distal tip 28. For example, where the second depth marking 110b is longitudinally spaced (proximally) a distance of 0.5 cm from the first depth marking 110a and the third depth marking 110c is spaced 0.5 cm from the second depth marking 110b, during use when the delivery cannula 36 is inserted within the guide cannula 22 such that the second depth marking 110b is aligned with the proximal side of the handle 30, a user can visually confirm (from a location away from the surgical site and outside of the patient) that an approximately 0.5 cm length of the delivery cannula 36 is extending distal the distal tip 28 of the guide cannula 22. Similarly, when the third marking 110c is aligned with the proximal side of the handle 30, an approximately 1.0 cm length of the delivery cannula 36 is exposed distal the distal tip 28. The indicial 110 can assume a wide variety of forms differing from that shown in FIG. 1, and in some embodiments can be eliminated.

Figure 4:
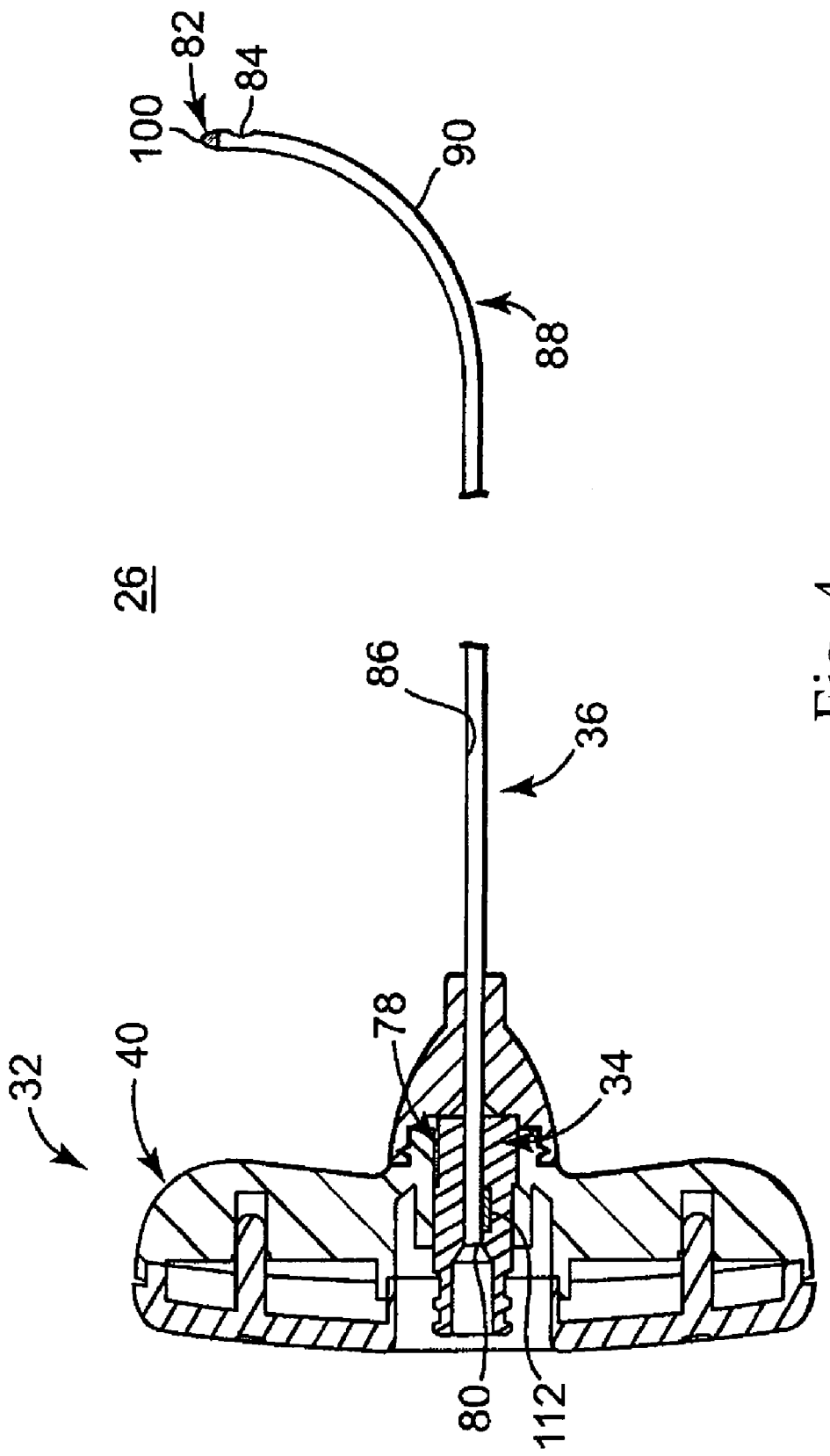
FIG. 4 is a cross-sectional view of the delivery cannula device of FIG. 2A upon final assembly.

With reference to FIG. 4, assembly of the delivery cannula device 26 includes first securing the hub 34 to the delivery cannula 36. In one embodiment, the hub 34 is overmolded onto the delivery cannula 36. To provide enhanced tensile strength at the hub 34/delivery cannula 36 interface, in one embodiment, a support body 112 is secured to the delivery cannula 36 adjacent the proximal end 80 (referenced generally) prior to forming/overmolding the hub 34. The support body 112 is preferably a rigid material amenable to affixment to the delivery cannula 36 material (e.g., where the delivery cannula 36 is formed of Nitinol, the support body 112 can also be formed of Nitinol and thus easily welded to the delivery cannula 36). The support body 112 can assume a variety of shapes and sizes, but in one embodiment, is rectangular (a thickness on the order of 0.035 inch, width on the order of 0.05 inch, and a length on the order of 0.2 inch, although other dimensions are equally acceptable) so that when applied to the otherwise circular (in transverse cross-section) delivery cannula 36, the support body 112 provides flat surfaces onto which the hub 34 is overmolded. This flat surface area interface, in turn, overtly resists "slipping" of the hub 34 relative to the delivery cannula 36 and vice-versa in response to a tensile, compressive, and/or torsional force(s) placed on either component. For example, in instances where the distal end 82 of the delivery cannula 36 is inserted or lodged within bodily material (e.g., bone or tissue) at a surgical site and a proximal pulling force is placed on the hub 34 (for example, via the handle 40), the delivery cannula 36 will not detach from the hub 34 even though the distal end 82 "resists" proximal movement (due to lodgment within the bodily material). Similarly, a rotational or torsional force placed upon the hub 34 will consistently translate onto the delivery cannula 36 via the hub 34/support piece 112 interface regardless of whether the distal end 82 "resists" rotational movement due to surgical site interactions. Alternatively, however, the support body 112 can be omitted and is not a necessary element.

Following attachment of the hub 34 to the delivery cannula 36, the hub 34 is mounted within the handle assembly 32 as previously described. For example, the hub 34 is nested within the aperture 56 of the handle 40, and the retainer 42 is coaxially disposed over the hub 34/delivery cannula 36 and secured (e.g., threadably engaged) to the handle 40. To this end, and in one embodiment, the hub 34 is oriented relative to delivery cannula 36 such that the flattened area 78 of the hub 34 "faces" a spatial direction of the bend 90. The previously described configuration of the handle assembly 32 thus dictates that upon assembly of the hub 34 to the handle 40, the bend 90 will also extend in a known spatial direction relative to the handle 40. Alternatively, a spatial direction of the bend 90 relative to the handle 40 can be visually determined following mounting of the hub 34 thereto. Regardless, in one embodiment and as best shown in FIG. 1, the handle assembly 32 further includes directional indicia 114 (referenced generally) along an exterior of the handle 40 that provides a user with an indication of the bend 90 direction relative to the handle 40. For example, in one embodiment, the directional indicia 114 includes an arrow 114a "pointing" at the direction of the bend 90. With this configuration, a user can readily ascertain a spatial positioning of the bend 90 relative to the handle 40 when the bend 90 is inserted within the confines of a surgical site (and thus not otherwise visible to the user). The directional indicia 114 can be applied at various locations along the handle 40 such as on both major faces (one of which is visible in FIG. 1) as well as a proximal end thereof, and can assume a variety of forms. In other embodiments, the directional indicia 114 can be eliminated. Regardless, following mounting of the hub 34 to the handle assembly 32, the delivery cannula device 26 can be used to deliver a curable material into bone.

In another preferred embodiment, the present invention includes a probe (not shown) in the form of a wire that can be inserted into the delivery cannula 26 to remove blockages that may form within the delivery cannula 26. Preferably, the probe has a diameter that is smaller than the inner diameter of the delivery cannula 26 to allow material within the delivery cannula 26 to flow around the probe as the probe is inserted into the delivery cannula 26. In one preferred embodiment, the probe is flexible enough to travel through the curvature of the delivery cannula 26, but still rigid enough to remove blockages within the delivery cannula 26.

Figure 5:
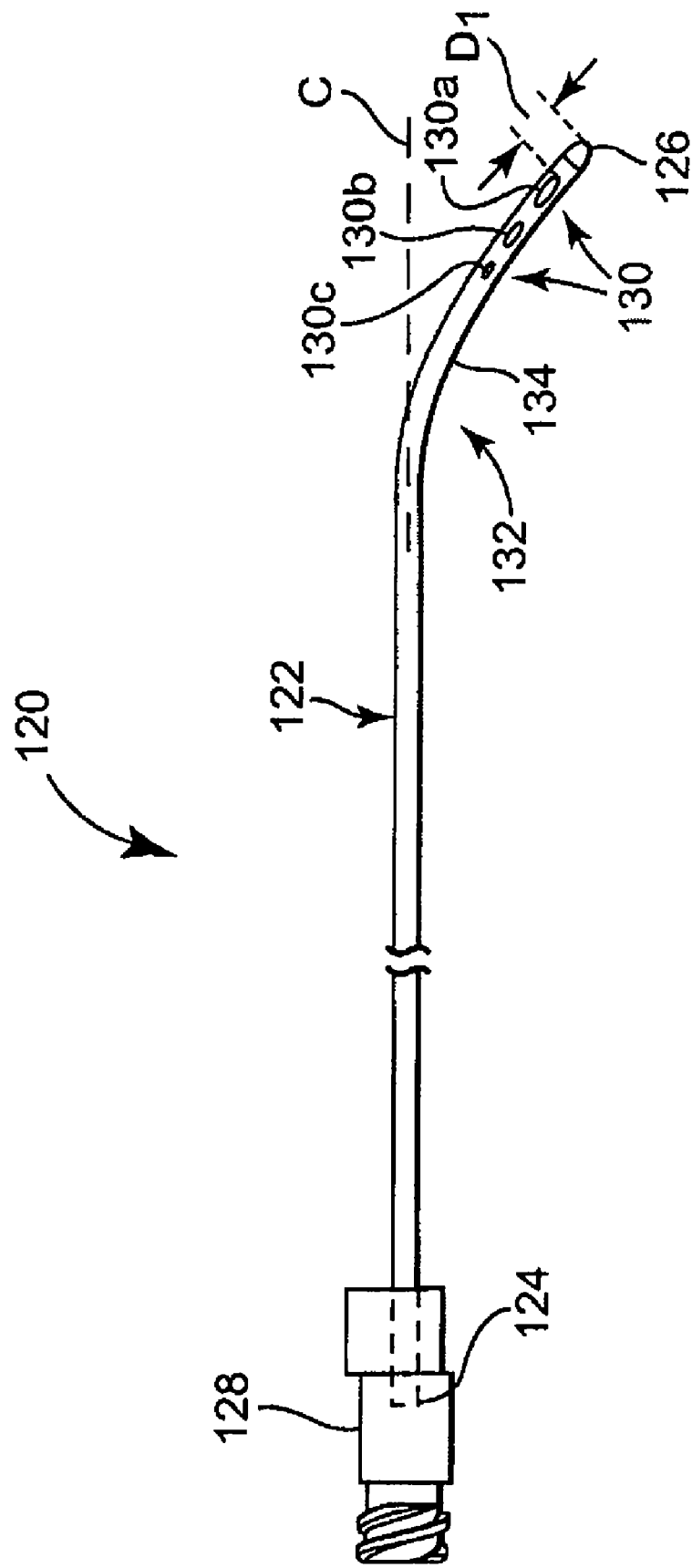
FIG. 5 is a side plan view of an alternative delivery cannula device in accordance with principles of the present invention.

Although the delivery cannula device 26 has been described as including the delivery cannula 36 otherwise forming one side orifice 84, a variety of other configurations are also acceptable. For example, two, circumferentially aligned side orifices can be provided. Further, FIG. 5 illustrates portions of another embodiment delivery cannula device 120 in accordance with principles of the present invention. The delivery cannula device 120 includes a delivery cannula 122 that extends a length between a proximal end 124 and a distal end 126, and a hub 128 coupled to the proximal end 124. The delivery cannula 122 is similar to the delivery cannula 36 (FIG. 2A) described above (including a blunt tip), but forms a series of longitudinally aligned side orifices 130, spaced along a length of the delivery cannula 122, and fluidly connected to an internal lumen (not shown). Further, the delivery cannula 122 includes a deflectable segment 132 forming a pre-set curve 134, similar to previous embodiments.

A distal-most side orifice 130a is offset the distance D1 from the distal end 116. Once again, the distance D1 is, in one embodiment, in the range of 0.05-0.5 inch, preferably in the range of 0.1-0.25 inch. A longitudinal spacing between the remaining side orifices 130 proximal the distal-most side orifice 130a can vary. Preferably, however, the second side orifice 130b defines a smaller sized opening as compared to the distal-most side orifice 130a, and the third side orifice 130c is smaller than the second side orifice 130b. This reduction in side orifice size proximal the distal end 126 promotes consistent distribution of curable material otherwise being forced through the delivery cannula 122.

While three of the side orifices 130 are shown, other configurations are also acceptable. For example, multiple side orifices (i.e., more than three side orifices) can be formed longitudinally along the length of the delivery cannula 122, and in addition, the side orifices 130 can include more than one longitudinally aligned series of side orifices. In an exemplary embodiment, the side orifices 130 that are visible in FIG. 5 are matched by another column of longitudinally aligned side orifices formed on an opposing side of the delivery cannula 122 (and therefore not visible in the view of FIG. 5). Aspects of the present invention provide for the side orifices 130 to define circular side orifices, non-circular side orifices, or a set of circular and non-circular side orifices.

As a point of reference, the pre-set curve 134 is curved away from a central axis C of the delivery cannula 122 such that the curvature of the pre-set curve 134 is less than the radius of curvature R of the pre-set curve 90 (FIG. 2A) previously described, thus illustrating another embodiment in accordance with principles of the present invention. In addition, while the side orifices 130 are depicted as formed along the pre-set curve 134, in another embodiment at least one of the side orifices 130 is formed proximal the pre-set curve 134.

Figure 5A:
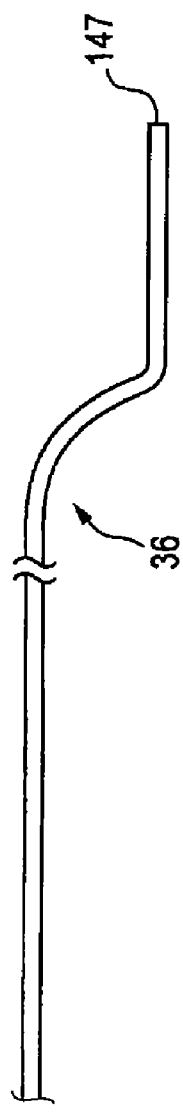
FIG. 5A is a side plan view of an alternative delivery cannula device in accordance with principles of the present invention.
Figure 5B:
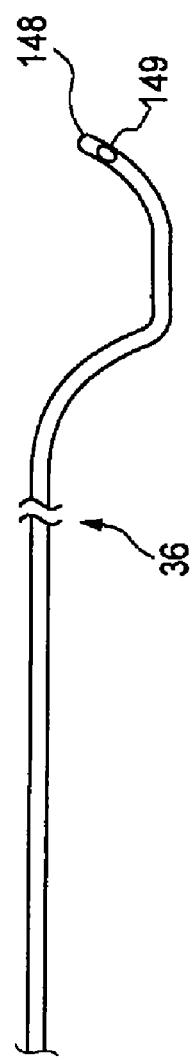
FIG. 5B is a side plan view of an alternative delivery cannula device in accordance with principles of the present invention.

In other preferred embodiments, the delivery cannula 36 can comprise multiple pre-set curves to allow better delivery of curable material within a cavity. With reference to FIGS. 5A and 5B, preferred additional delivery cannula configurations are shown. In each of these configurations with multiple pre-set curves, the delivery cannula can comprise an open end 147 or a closed end 148 and contain one or more side orifices 149. A delivery cannula having multiple preset curves can be shaped according to the methods described previously herein and have a shape memory characteristic.

Figure 6A:
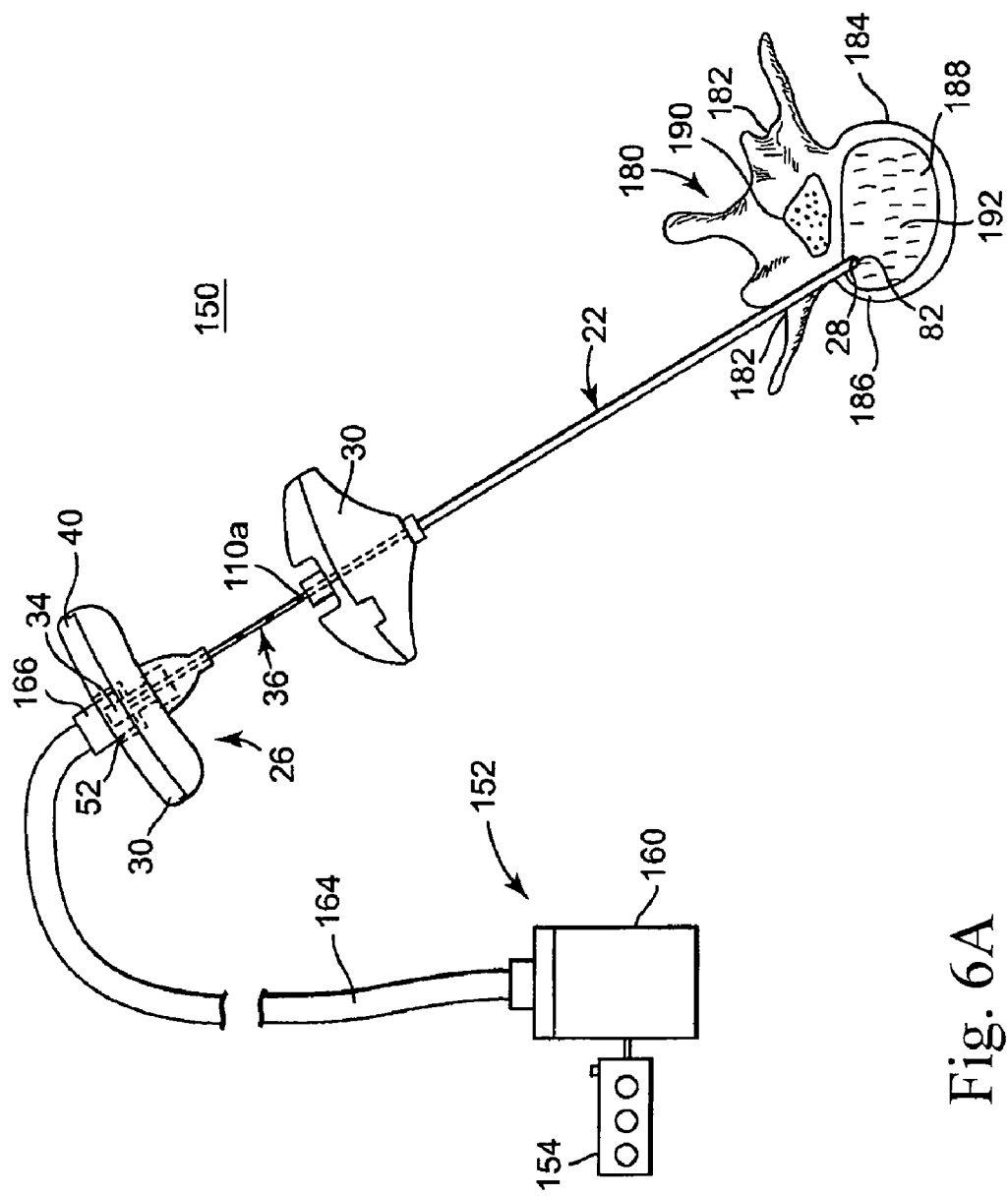
FIG. 6A is a simplified plan view of an intraosseous curable material delivery system employed in a palliative bone procedure in accordance with principles of the present invention.

Regardless of an exact configuration, the assembled delivery cannula device (such as the delivery cannula device 26 of FIG. 4) in accordance with principles of the present invention is highly useful in performing a wide variety of bone stabilizing procedures as part of an overall curable material delivery system. To this end, FIG. 6A illustrates an intraosseous curable material delivery system 150 according to one embodiment of the present invention, employed to perform a vertebroplasty procedure. The system 150 includes the outer guide cannula 22, the delivery cannula device 26, a curable material source 152 fluidly coupled to the delivery cannula device 26, and a controller 154 coupled to at least the curable material source 152.

The curable material source 152 includes, in one embodiment, a canister 160 containing a curable material as previously described, and tubing 164 extending from the canister 160 to the handle assembly 30 of the delivery cannula device 26. In this regard, the tubing 164 terminates at a fitting 166 configured to removably attach to the hub 34. In particular, the fitting 166 is configured to fit within the passage 52 of the handle 40 and removably couple to the hub 34. In one embodiment, the fitting 166 threads onto a Luer thread defined by the hub 34. In another embodiment, the fitting 166 snap-fits over the hub 34. Alternatively, a wide variety of other attachment configurations are also available.

The controller 154 can assume any form known in the art and is coupled to the curable material source 152. In an exemplary embodiment, the controller 154 controls a mass flow and a mass flow rate (i.e., a fluid delivery rate) of curable material from the canister 160 to the delivery cannula device 26. The controller 154 can include a variety of actuators (e.g., switch(es), foot pedal(s), etc.) affording a user the ability to remotely control liquid flow into the delivery cannula 36. Alternatively, manual control can be employed such that the controller 154 can be eliminated.

During a palliative bone procedure, with the delivery cannula 36 partially retracted within, or entirely removed from, the outer guide cannula 22, the outer guide cannula 22 is located at a desired delivery site within bone. For example, in a vertebroplasty procedure the outer guide cannula 22 is introduced into a vertebra 180, preferably at a pedicle 182. In this regard, the vertebra 180 includes a vertebral body 184 defining a vertebral wall 186 surrounding bodily material (e.g., cancellous bone, blood, marrow, and other soft tissue) 188. The pedicle 182 extends from the vertebral body 184 and surrounds a vertebral foramen 190. In particular, the pedicle 182 is attached posterior to the vertebral body 184 and together they comprise the vertebrae 180 and form the walls of the vertebral foramen 190. As a point of reference, the intraosseous system 150 is suitable for accessing a variety of bone sites. Thus, while a vertebra 180 is illustrated, it is to be understood that other bone sites can be accessed by the system 150 (i.e., femur, long bones, ribs, sacrum, etc.).

The outer guide cannula 22 forms an access path to a delivery site 192 (or forms the delivery site 192) through the pedicle 182 into the bodily material 188. Thus, as illustrated, the outer guide cannula 22 has been driven through the pedicle 182 via a transpedicular approach. The transpedicular approach locates the outer guide cannula 22 between the mammillary process and the accessory process of the pedicle 182. In this manner, the outer guide cannula 22 provides access to the delivery site 192 at the open, distal tip 28. With other procedures, the outer guide cannula 22 can similarly perform a coring-like operation, forming an enlarged opening within bone. In one preferred embodiment illustrated in FIG. 6A, the distal tip 28 of the guide cannula 22 is positioned close to the entrance point into the delivery site 192. As will be explained in more detail herein, the smaller the projection of the distal tip 28 into the delivery site 192 allows for greater access for the delivery cannula 36 to be positioned within the delivery site 192 and deliver curable material to desired locations within the delivery site 192.

Once the outer guide cannula 22 has formed, or is otherwise positioned within bone at, the desired delivery site 192, the delivery cannula 36 is slidably inserted/distally advanced within the outer guide cannula 22. As illustrated generally in FIG. 6A, the distal end 82 of the delivery cannula 36 is poised at the distal tip 28 of the outer guide cannula 22. Approximate alignment of the first depth marking 110a with the handle 30 provides a user with visual confirmation (at a point outside of the patient) of the distal end 82 positioning relative to the outer guide cannula 22 distal tip 28. Prior to further distal movement, the delivery cannula 36 is entirely within the outer guide cannula 22 such that the deflectable segment 88 (FIG. 2A) of the delivery cannula 36 is constrained (i.e., flexed) to a substantially straightened shape that generally conforms to a shape of the outer guide cannula 22. This relationship is shown more clearly in FIG. 6B whereby a force is effectively imparted by the guide cannula 22 onto the deflectable segment 88 due to the radius of curvature R (FIG. 2A) defined by the deflectable segment 88 in a "natural" state being larger than an inner diameter of the guide cannula 22. This interaction essentially "removes" the pre-set curvature of the bend 90 (FIG. 2A), forcing or rendering the deflectable segment 88 to a substantially straightened state (it being understood that because an inner diameter of the guide cannula 22 is greater than the outside diameter of the delivery cannula 36, the deflectable segment 88 will continue to have a slight curvature within in the guide cannula 22; thus, "substantially straightened" is in reference to the delivery cannula 36 being substantially, but not necessarily entirely, linear). Thus, prior to interaction with the delivery site 192 (FIG. 6A), the delivery cannula 36 is flexed in a substantially straight, non-curved orientation within the outer guide cannula 22.

Figure 6C:
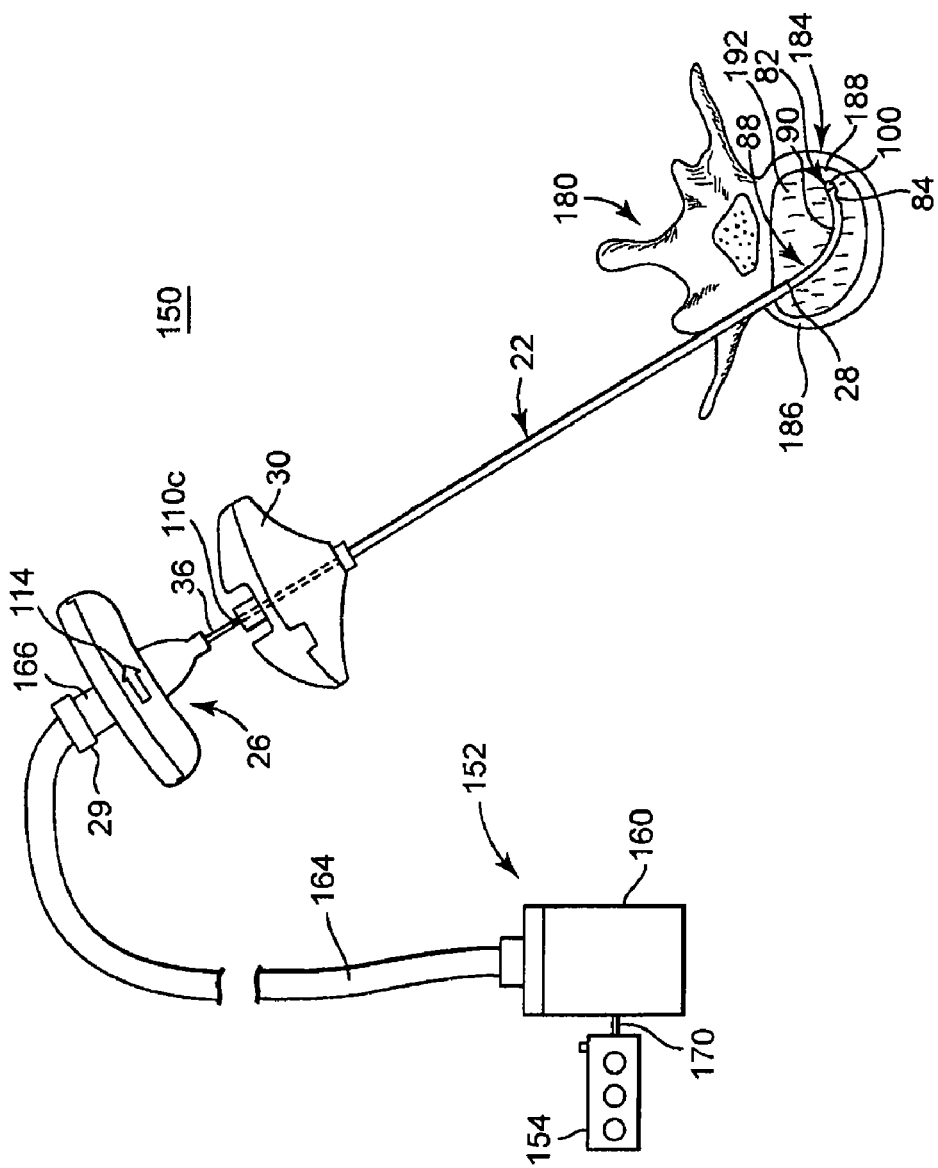
FIG. 6C illustrates a final stage of a procedure performed by the system of FIG. 6A.

The delivery cannula device 26, and in particular the delivery cannula 36, is then distally advanced within the guide cannula 22 as shown in FIG. 6C. In particular, the delivery cannula 36 is distally maneuvered such that at least a portion of the deflectable segment 88 extends beyond the open tip 28 of the guide cannula 22 and into the delivery site 192. The now unrestrained portion of the deflectable segment 88 naturally deflects laterally (from the substantially straight shape described above) upon exiting the guide catheter 22, reverting to the pre-set curvature of the bend 90 previously described due to the shape memory characteristic. The user can visually confirm a length of distal extension of the delivery catheter 36 from the guide catheter 22 via a longitudinal positioning of the indicia 110b or 110c (the indicia 110c being visible in FIG. 6C) relative to the handle 30. Further, the directional indicia 114 indicate to a user (at a point outside of the patient) a spatial direction of the bend 90 within the delivery site 192 relative to a spatial position of the handle 40.

In connection with distal advancement of the delivery cannula 36, the blunt tip 100 of the distal end 82 is hemispherically shaped (or other non-sharpened or blunt shape) and thus atraumatic relative to contacted tissue/bone. In this manner, the blunt tip 100 can contact and/or probe the vertebral wall 186 with a minimum of risk in puncturing or coring the vertebral body 184. Thus, the blunt tip 100 offers an advantage over the conventional, sharp-edged bone cement delivery needles, and does not require a separate wire to prevent coring as is otherwise necessary with available curved needles.

The side orifice 84 is offset from the distal end 82 and is, therefore, available to deliver curable material into, and remove bodily material from, the delivery site 192. In particular, the side orifice 84 can eject curable material radially from, and aspirate bodily material into, the delivery cannula 36, even when the distal end 82 is pressed against a surface, such as an interior wall of the vertebral body 184.

Figure 6D:
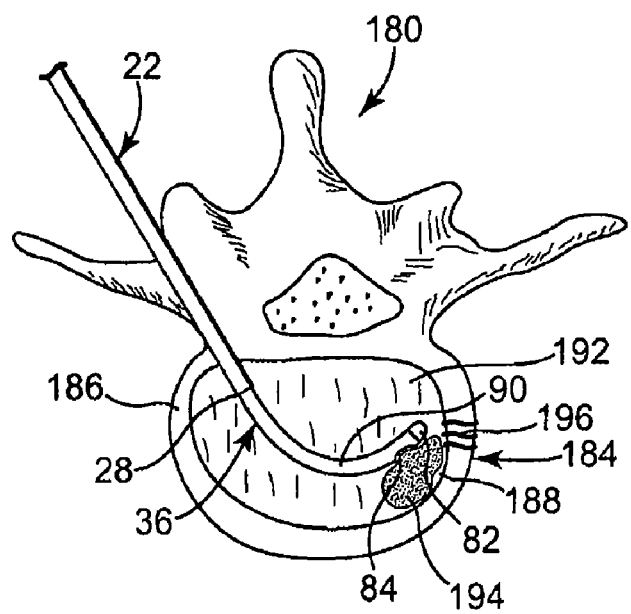
FIG. 6D is a transverse, sectional view of a vertebral body in combination with a portion of the system of FIG. 6A, illustrating injection of curable material.

With the above in mind, in one embodiment, the fluid source 152 is then operated (e.g., via the controller 154) to deliver a curable material (not shown) to the delivery cannula 36 via the hub 34. Curable material entering the delivery cannula 36 is forced through the lumen 86 (FIG. 2A) towards the side orifice 84. As shown in FIG. 6D, the curable material is then dispensed/injected from the delivery cannula 36 in a radial fashion from the side orifice(s) 84 and into the delivery site 192 in a cloud-like pattern 194. Alternatively or in addition, the delivery site 192 can be aspirated by replacing the curable material source 152 (FIG. 6A) with a vacuum source (not shown).

In another embodiment, curable material is delivered to the delivery cannula 36 prior to introducing the delivery cannula 36 into the guide cannula 22. In practice, an operator may advance curable material beyond the side orifice(s) 84 the delivery cannula 36 in order to completely fill the delivery cannula 36 and then wipe the side orifice(s) 84 of excess curable material before insertion into the guide cannula 22. The delivery cannula 36 is thus preloaded with curable material before the delivery cannula 36 is connected with the guide cannula 22. Once the delivery cannula 36 is inserted into the guide cannula 22 curable material is immediately available to be delivered into the implantation site. This preloading step advantageously reduces the time required to deliver curable material into a patient because it can be done at substantially the same time the guide cannula 22 has being driven into the delivery site.

Importantly, by injecting the curable material radially from a side of the delivery cannula 36 rather than axially from the distal most end (as will otherwise occur with conventional delivery needles), the system 150 (FIG. 6A) can avoid forcing the curable material into a fracture or other defect that may in turn lead to undesirable leaking of the curable material through the fracture. By way of example, FIG. 6D illustrates a fracture 196 in the vertebral body wall 186. Vertebroplasty is a common solution to such vertebral fractures, with the accepted repair technique entailing positioning the distal end 82 at or "facing" the fracture 196 to ensure that the curable material is dispensed in relatively close proximity thereto. With known delivery needles, this preferred approach results in the curable material being injected directly toward the fracture 196. In contrast, with the delivery catheter 36 of the present invention, the distal end 82 is still "facing" the fracture 196, yet the injected curable material cloud 194 is not forced directly toward the fracture 196. Instead, the curable material cloud 194 indirectly reaches the fracture 196 with minimal retained propulsion force such that the curable material cloud 194 is unlikely to forcibly "leak" through the fracture 196. However, the delivery site 192 is, as a whole, still filled with the curable material cloud 194 to effectuate the desired repair.

Figure 6E:
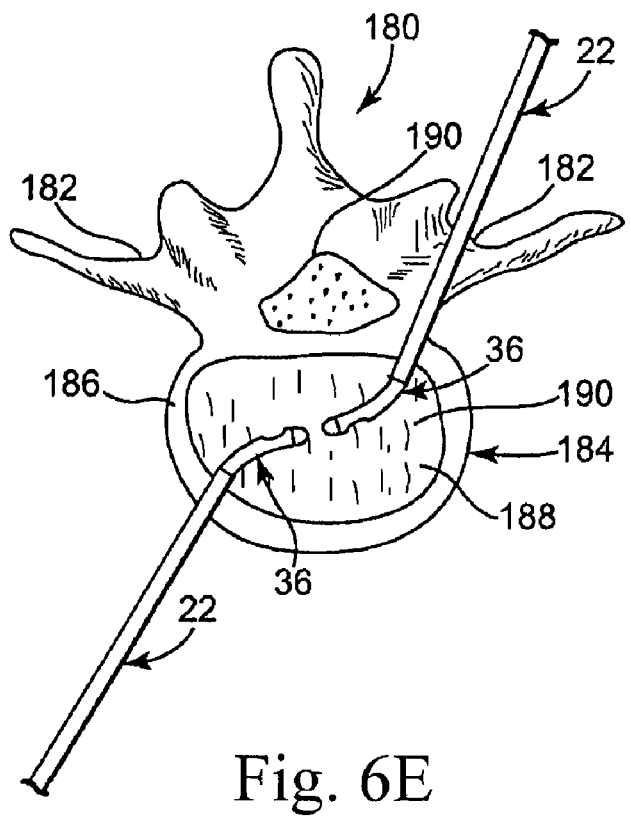
FIG. 6E is a transverse, sectional view of a vertebral body illustrating various vertebroplasty approach positions available in accordance with principles of the present invention.
Figure 7A:
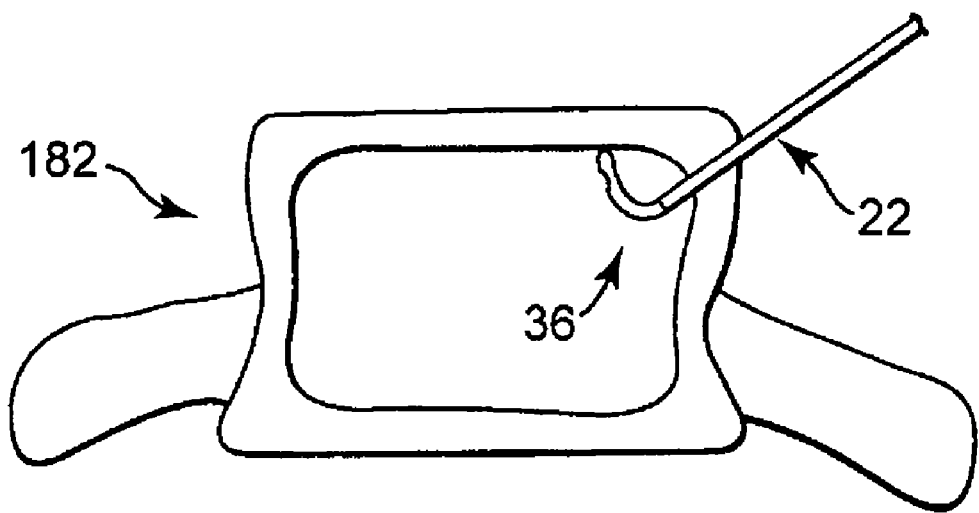
FIGS. 7A and 7B are simplified anterior views of a vertebral body, illustrating use of the system in accordance with principles of the present invention.
Figure 7B:
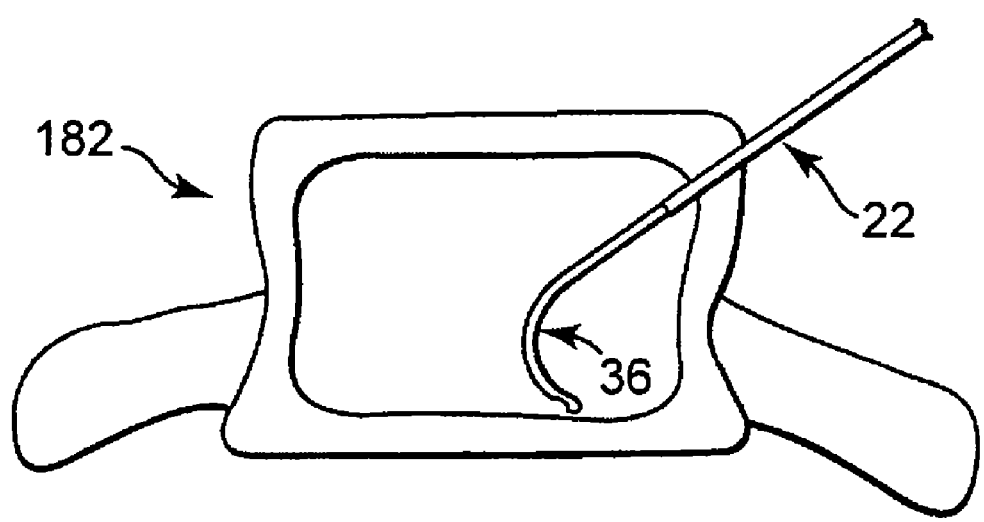

As shown in FIG. 6D, an entirety of the delivery site 192 is accessible by the delivery cannula 36. To this end, while the guide cannula 22 has been inserted via a right posterior-lateral approach, the system 150 can effectuate a vertebroplasty procedure from a left posterior lateral approach, or to right or left anterior lateral approaches as shown in FIG. 6E.

In one embodiment, and returning to FIG. 6C, a desired volume of the curable material is delivered entirely through the delivery cannula 36. In other embodiments in accordance with principles of the present invention, after injecting a first volume of curable material through the delivery cannula 36, the delivery cannula 36 is disconnected from the curable material source 152 and removed from the guide cannula 22. The curable material source 152 is then fluidly connected to the guide cannula 22 (e.g., the fitting 166 is fluidly connected to a corresponding fluid port/hub provided with the handle 30) and then operated to inject a second volume of curable material to the delivery site 192 via the guide cannula 22.

In another preferred embodiment, the tubing 164 supplying curable material is rotatably coupled to the delivery cannula device 26. With further reference to FIG. 6C, in this embodiment an optional rotatable connector 29 is located between the delivery cannula 26 and the source 152 of curable material to allow the delivery cannula 26 and source 152 of curable material to rotate with respect to each other. Rotatable connectors suitable for curable material delivery devices are described in U.S. patent application Ser. No. 11/526,164, incorporated herein by reference with respect to its disclosure of the rotatable connectors. In this embodiment, the rotatable connector 29 allows a physician to rotate the delivery cannula 26, and thus rotate the curved end of the delivery cannula 26 within the implantation site, without requiring the source of curable material to be disconnected from the delivery cannula 26 or rotated with respect to the delivery cannula. In a preferred embodiment, the rotatable connector 29 is operative to rotate the delivery cannula 26 preferably about 90 degrees and more preferably about 360 degrees.

Figure 8A:
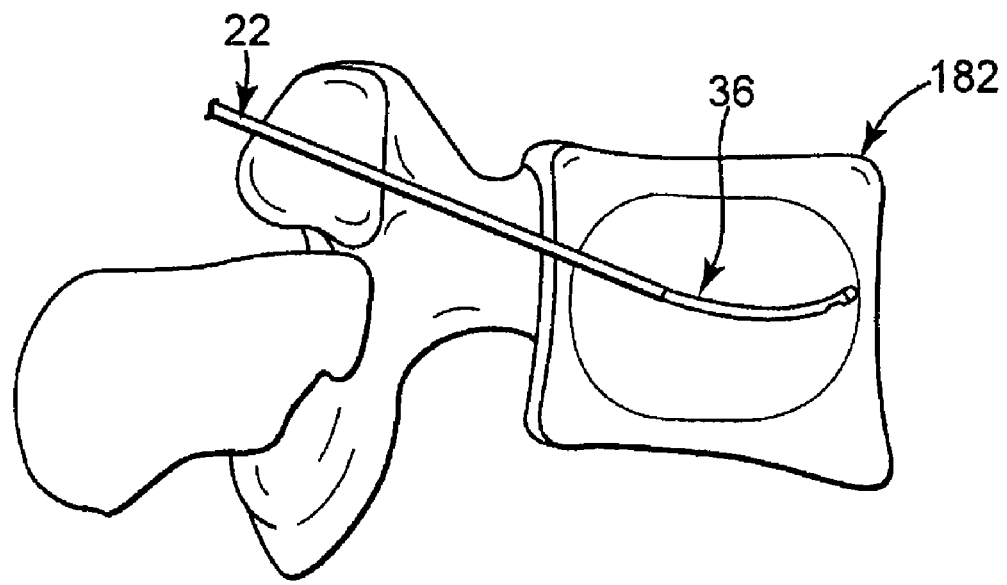
FIGS. 8A and 8B are simplified lateral views of a vertebral body, illustrating use of the system in accordance with principles of the present invention.
Figure 8B:
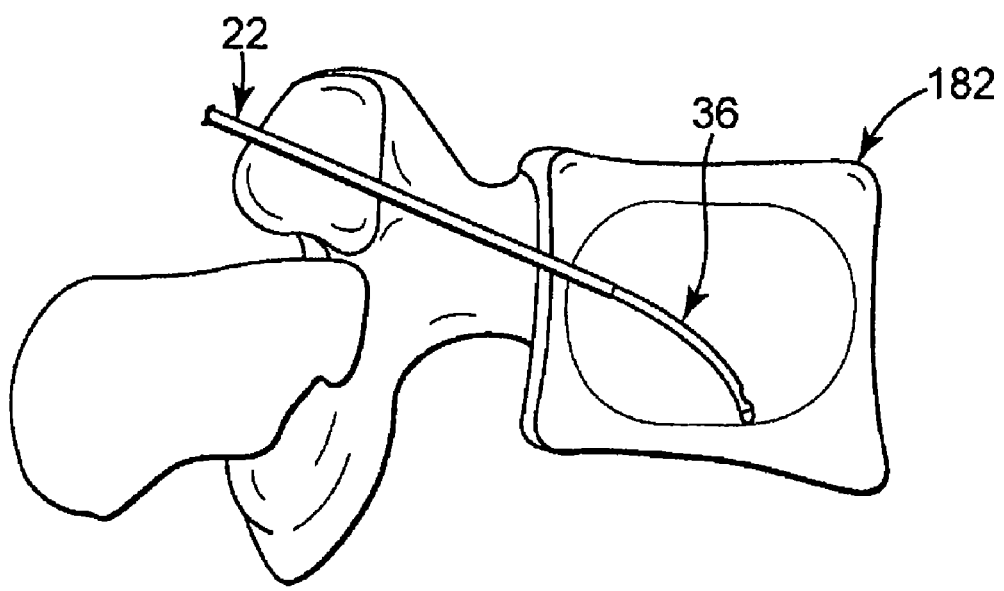

In more general terms, during the palliative bone procedure, a clinician operating the intraosseous system 150 extends a portion of the pre-set curve 90 into the delivery site 192 otherwise defined within bone. In one embodiment, a subsequent rotation of the delivery cannula 36 rotates a spatial position of the side orifice 84 relative to the delivery site 192, thus accessing multiple planes of the delivery site 192 with only one "stick" of the outer guide cannula 22. Thus, by a combination of retracting the delivery cannula 36 within the outer guide cannula 22, distally advancing the delivery cannula 36 relative to the outer guide cannula 22, and by rotating the delivery cannula 36, multiple planes and multiple regions of the bone site of interest can be accessed by the delivery cannula 36 with a single approach of the outer guide cannula 22. Thus, for example, a unipedicular vertebroplasty can be accomplished with the system 150. FIGS. 7A-8B generally illustrate (FIGS. 7A and 7B from an anterior perspective; FIGS. 8A and 8B from a left lateral perspective) various planes/regions of the vertebral body 182 accessible with rotation and/or advancement of the delivery cannula 36 relative to the guide cannula 22 (again with the guide cannula 22 remaining stationary). Notably, in the drawings of FIGS. 7A-8B, a direction of the bend defined by the delivery cannula 36 is not necessarily perpendicular to the plane of the page, such that the bend may not be fully evident in each view.

Figure 9:
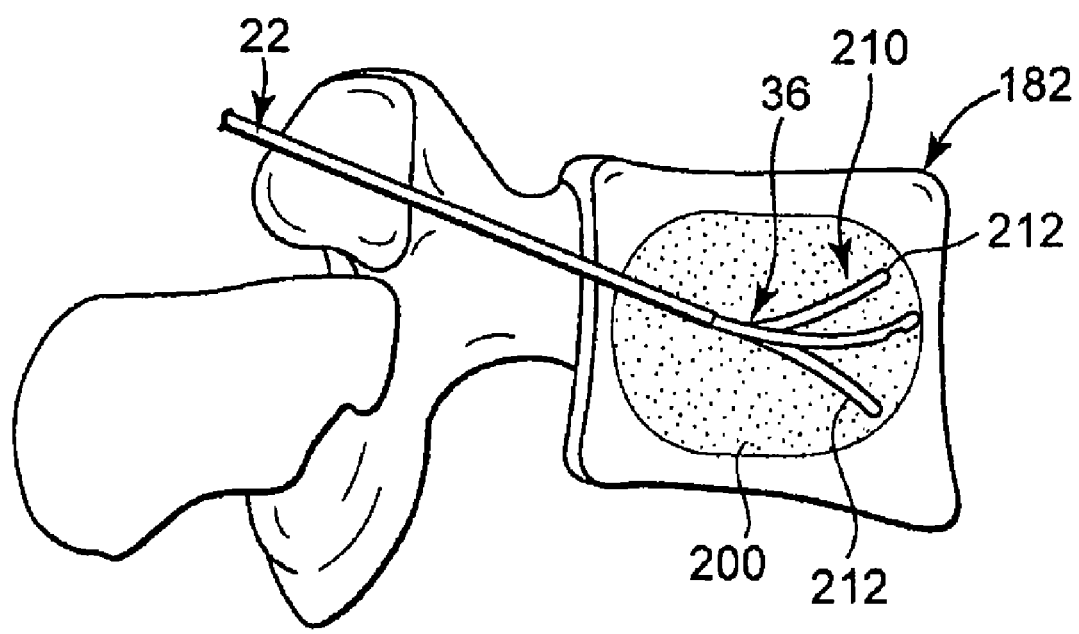
FIG. 9 is a simplified lateral view of a vertebral body, illustrating use of the system in accordance with principles of the present invention.
Figure 10:
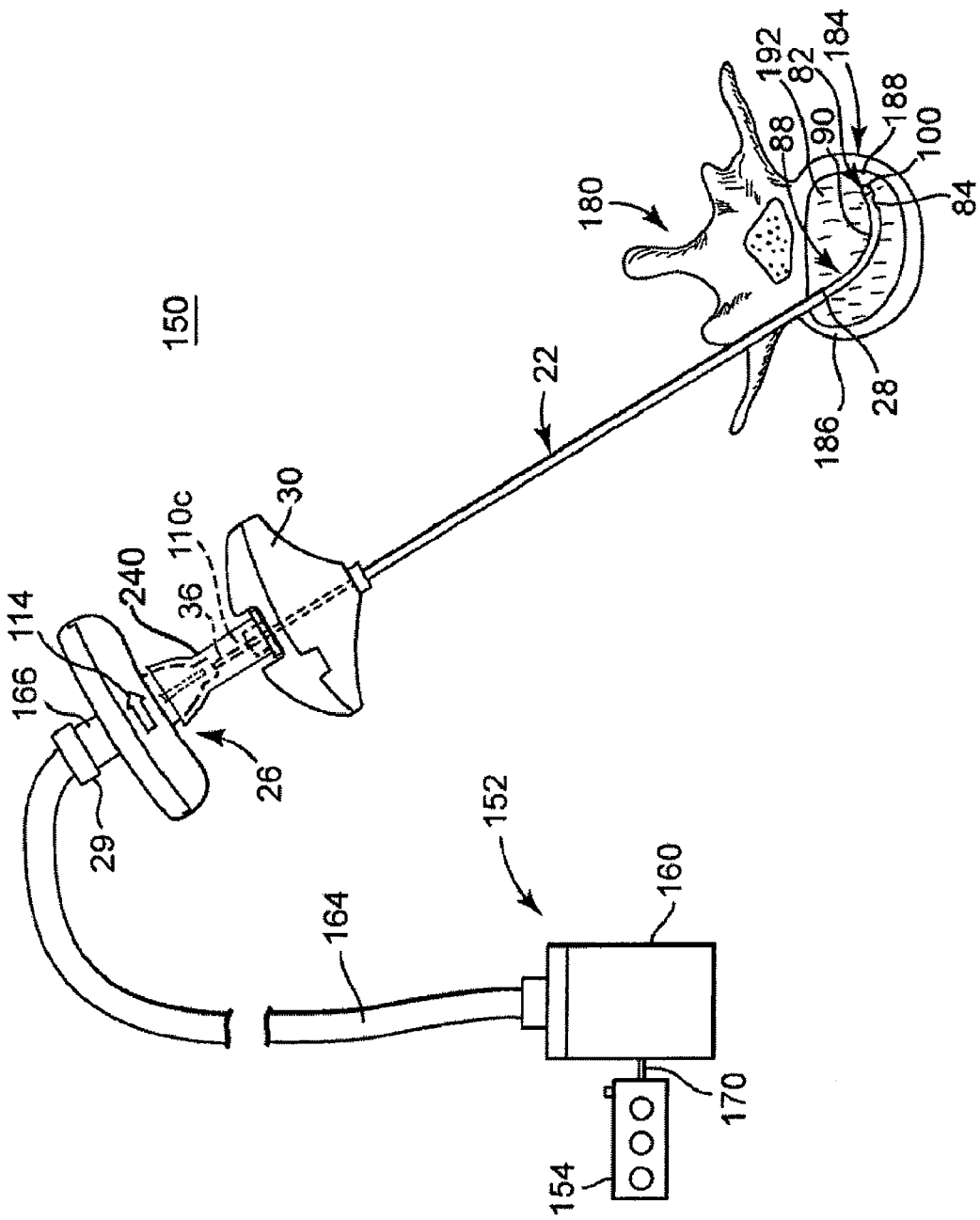
FIG. 10 is a simplified plan view of an intraosseous curable material delivery system including a spacer element and employed in a palliative bone procedure in accordance with principles of the present invention.

With reference to FIGS. 9-10C, another preferred method for delivering curable material is depicted. In this preferred embodiment, a clinician creates voids 210 in soft body material 200 (e.g., cancellous bone, blood, marrow, and other soft tissue) within a bone delivery site by manipulating the curved end 90 of the delivery cannula 36. The voids 210 can then be filled with curable material. It has been observed that when voids are created, curable material delivered to the delivery site will generally flow into the voids 210 instead of the soft body material 200. As a result, a clinician can create a void 210 at a relatively small desired area, and fill primarily just that area with curable material.

FIG. 10 is similar in all respects to FIG. 6C, except that includes a spacer element 240 (but may include, e.g., spacer 260, or each in turn, potentially with one or more other spacers in cooperation or in turn). Accordingly, reference is made thereto and to the corresponding sections of this specification for the operations shown in FIG. 10. The exception is that a method of using the system with a spacer element includes disposing the spacer 240 about the delivery cannula 36 and engaging it to the handle 40. In this manner, the distance to which the distal curved cannula end 90 extends past the vertebral wall 186 into the internal material 188 is controlled as described below with reference to FIGS. 10A-10C.

According to one preferred embodiment, voids can be created through a combination of retracting the delivery cannula 36 within the outer guide cannula 22 and distally advancing the delivery cannula 36 relative to the outer guide cannula 22, thus moving the curved end 90 in a reciprocating manner. The reciprocating action causes the curved end 90 to crush the soft body tissue and create a channel 212 within the soft body material. Additionally, by retracting the delivery cannula 36 within the outer guide cannula 22 and rotating the delivery cannula 36 so that the curved end 90 will distally advance within the delivery site at a different orientation, the curved end 90 can create multiple channels 212 within the soft body tissue 200. Further, the curved end 90 of delivery cannula 36 may be advanced distally only partially within the delivery site and then removed to create shorter channels 212 within the implantation site where desired.

According another preferred embodiment shown in FIGS. 10A-10C, the delivery cannula 36 can be rotated or spun after the curved end 90 has been introduced into the implantation site. The rotating or spinning of the delivery cannula 36 causes the curved end 90 to rotate or spin within the delivery site and whip through soft body tissue 200 to create a cone-shaped void 214 in the soft tissue 200 within the delivery site. Cone-shaped voids 214 of various sizes may be created by only partially inserting the curved end 90 into the implantation site and rotating the delivery cannula 36.

This can be accomplished in a controlled manner using spacers 240, 260. FIG. 10A shows a first portion of a void 210 being created by rotation of the delivery cannula 36, with a first, longer spacer (e.g., spacer 260) being disposed between the delivery cannula handle 40 and the guide cannula 22. FIG. 10C shows a second portion of a void 210 being created (and enlarging the first portion) by rotation of the delivery cannula 36, with a second, shorter spacer (e.g., spacer 240) being disposed between the delivery cannula handle 40 and the guide cannula 22. The difference between the spacer lengths provides a different center of rotation for the curved cannula portion 90 that can be selected by a user who chooses two or more spacers of desired lengths depending upon his assessment of the available space and desirable procedure. FIG. 10B shows the "second portion" of the void 210 as it would be created by rotation of the delivery cannula 36, with the second, shorter spacer (e.g., spacer 240) being disposed between the delivery cannula handle 40 and the guide cannula 22, without creation of the other void portion. Of course, one may create that second, deeper void portion first, and then proceed to create the "dual void" (which may actually include two separate voids, depending upon spacing and the delivery cannula size) shown in FIG. 10C.

Voids 210 within the soft body tissue of various sizes and shapes can be created by using a combination of the above disclosed methods. According to one preferred method, a physician may introduce curable material within the implantation site as he or she is creating the voids within the implantation site. Thus, the voids may be created and filled at the same time. As a precursor step to the above methods, a physician may determine measurements of a bone to be treated and select one, two, or more spacers that will provide for voids at desired positions within a region of the bone to be treated.

One skilled in the art will appreciate that whether voids are first created and then filled, or curable material is delivered in a cloud-like pattern without first creating voids, the delivery cannula of the present invention can be manipulated to deliver small deposits of curable material to specific desired areas within a cavity.

Figure 11A:
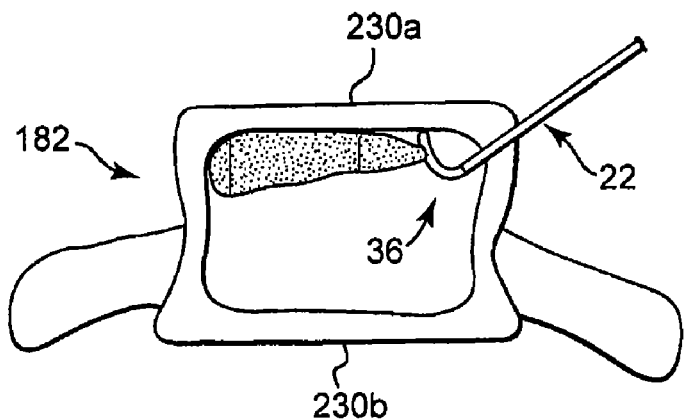
FIGS. 11A-11C are simplified anterior views of a vertebral body, illustrating use of the system in accordance with principles of the present invention.
Figure 11B:
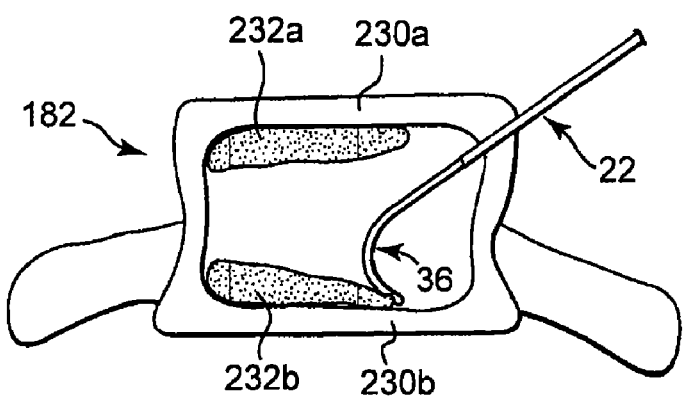

In one embodiment, curable material can be delivered in different planes to form curable material structures within the cavity to stabilize the endplates of the vertebral body, as depicted in FIGS. 11A and 11B. In one preferred embodiment, curable material 232a and 232b is deposited proximal to the endplates 230a and 230b of the vertebral body so that the curable material substantially interfaces with the endplates 230a and 230b and provides structural support. According to one preferred embodiment, the procedure leaves a region between the curable material deposits 232a and 232b that contains substantially no curable material. Curable material can thus be deposited in only a particular region or regions of the cavity.

Figure 11C:
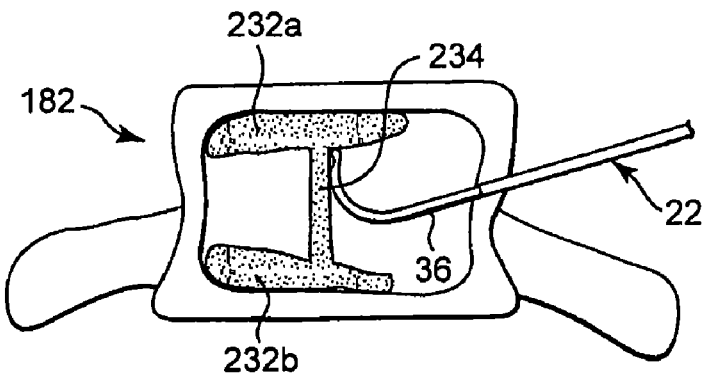

With reference to FIG. 11C, in another preferred embodiment the curable material deposits 232a and 232b can be connected by placing curable material between the curable material deposits 232a and 232b to form a curable material stabilizing column 234. In this embodiment, curable material deposits 232a and 232b are first created to stabilize the endplates of the vertebral body. A stabilizing curable material column 234 is then created between the curable material deposits 232a and 232b to connect the curable material deposits and form a curable material structure within the vertebral body. By first stabilizing the end plates, deformities created due to compression fractures can be stabilized. By stabilizing both end plates and then creating a column type structure between the end plates, the vertebral body stiffness may be significantly improved thereby minimizing issues of the overall strength of the vertebral body. It has been observed that depositing curable material in the known methods of depositing material in the center of the vertebral body, as typically created by a kyphoplasty procedure, or dispersed throughout the vertebral body, as typically created by a vertebroplasty procedure, do not uniformly strengthen the vertebral body. Because the cement is concentrated in regional areas, there is only minimal stabilization of the end plates. By stabilizing both end plates and then providing a structure to secure them together, the repaired vertebral body stiffness will better approximate the normal stiffness of a non-fractured vertebral body when compared to the known vertebroplasty or kyphoplasty procedures. In another preferred embodiment, if the compression fracture is more pronounced on one end plate, stabilization of only that one end plate may be necessary and only one curable material deposit will be created proximal to the vertebral endplate. In this embodiment, a support structure may be created to connect the curable material deposit and the vertebral endplate opposite the vertebral endplate being repaired.

Figure 12:
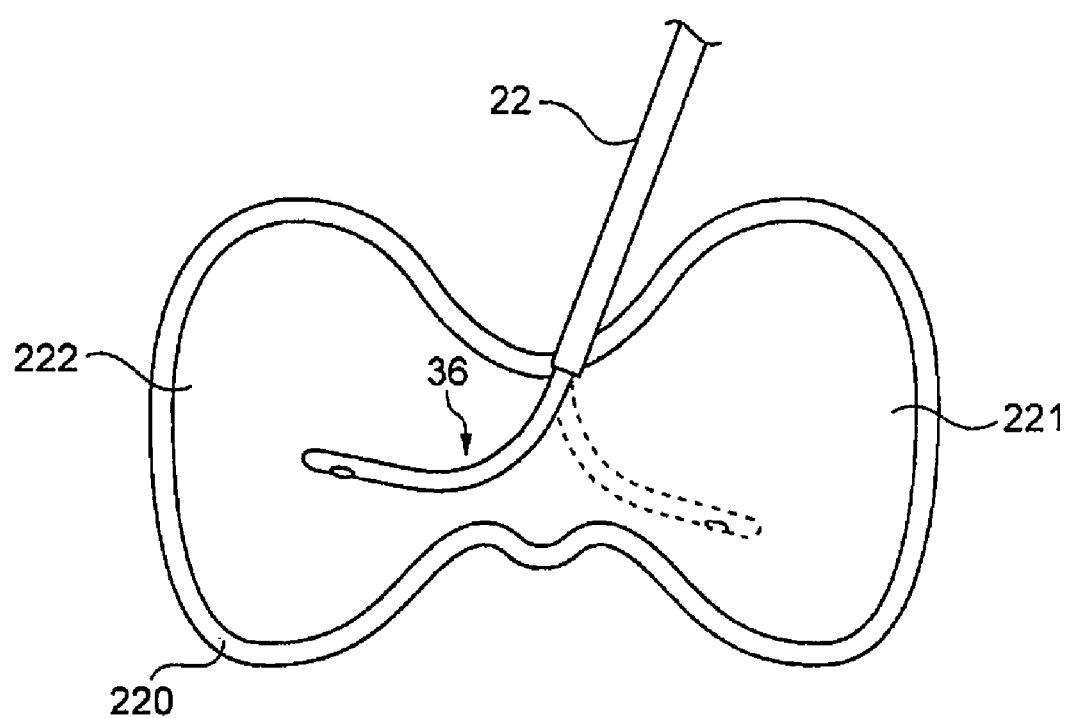
FIG. 12 is a simplified anterior view of a sacrum, illustrating use of the system in accordance with principles of the present invention.

With reference to FIG. 12, another preferred method for delivering curable material is depicted. In this preferred embodiment, the delivery site is the sacrum 220. In this embodiment, curable material is delivered to the sacrum 220 to repair bone fragments or fractures in the sacrum. According to one preferred method of the present invention, curable material is delivered to multiple regions within the sacrum through a single access point. Preferably, a guide cannula 22 is inserted generally at the middle portion of the sacrum. As has been described above, a curved needle is inserted into and advanced relative to the guide cannula 22. The delivery cannula 36 is preferably oriented so the curved end 90 enters proximal to a first region 221 of the sacrum 220. Curable material is then delivered to the first region 221 of the sacrum 220. After curable material is delivered to the first region 221, the physician can then partially or fully retract the curved end 90 within the guide cannula and then re-orient the delivery cannula 36 and curved end 90. As the delivery cannula 36 is again advanced relative to the guide cannula 22, the curved end 90 enters proximal to a second region 222 within the sacrum 220. Curable material is then delivered to the second region 222 of the sacrum 220. The process can be repeated for other additional regions. Although the implantation site described above is the sacrum, fractures in other bones can be repaired by delivering curable material to multiple regions through the same access point using the above described methods.

Figure 13A:
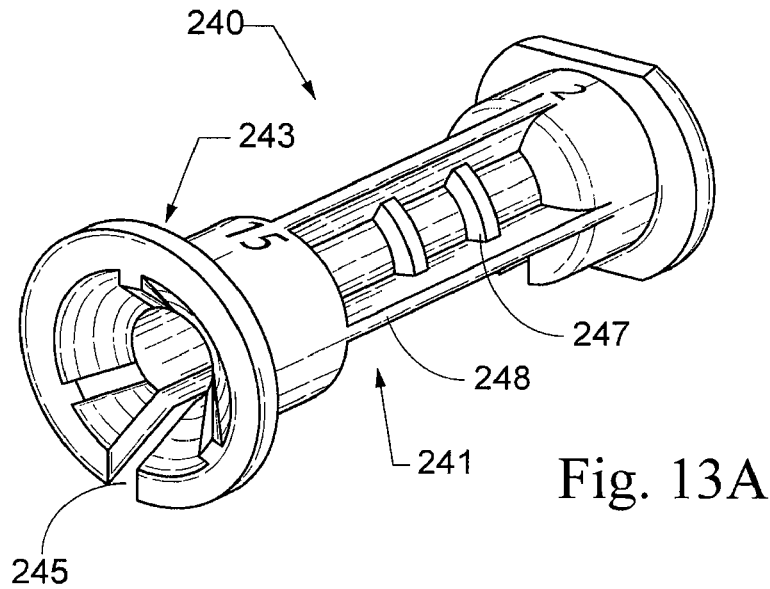
FIGS. 13A-13B show one spacer embodiment.
Figure 13B:
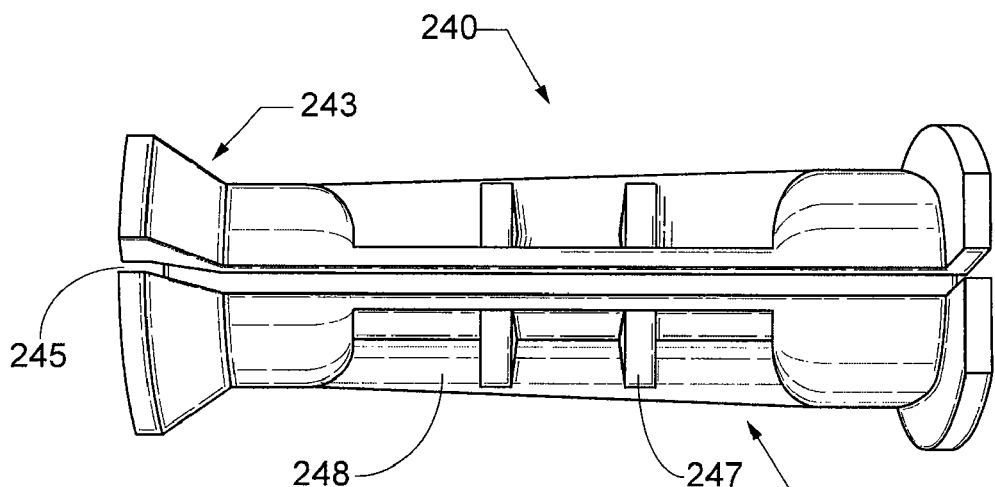
Figure 14:
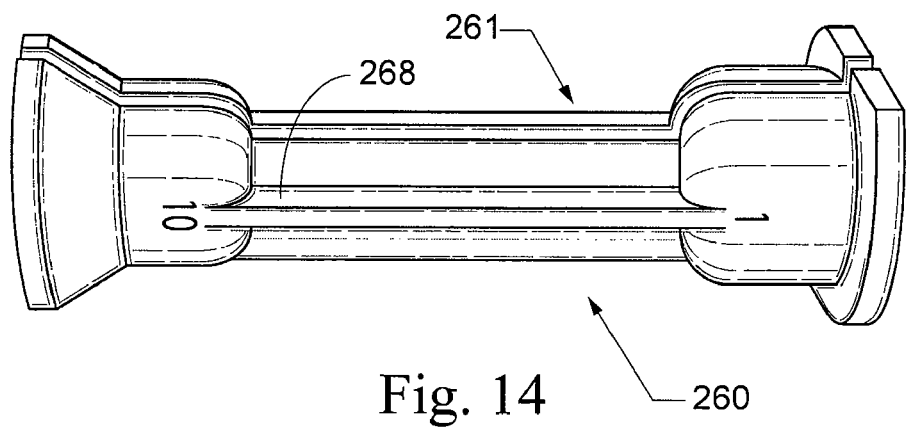
FIG. 14 shows another spacer embodiment.

FIGS. 13A-13B show the shorter spacer 240 and longer spacer 260, each having a predetermined length. The shorter spacer has a generally cylindrical body 241 that is flared at its proximal end 243. The proximal flare 243 includes detent ribs 242 configured to engage the detent grooves 43 of the delivery cannula handle 40. In one preferred embodiment, this detent interaction will provide both longitudinal engagement/retention of the spacer 240 with the handle 40 and will prevent rotation therebetween about their longitudinal axes. The spacer 240 has a predetermined length corresponding to and configured to control the distance to which a corresponding delivery cannula 36 will be allowed to extend beyond the distal end of a corresponding guide cannula 22 as described above. An elongate opening 245 along one side allows a user easily to mount the spacer 240 around the delivery cannula 36 and slide it up to engage the handle 40 (i.e., without having to thread it over the end). This feature provides for great ease of use with adding and removing spacers during a procedure using only one hand. This and other spacer embodiments may include one or more types of visual and/or tactile indicia to differentiate and identify the spacers (individually, or relative to other spacers).

For example, the shorter spacer 240 includes a numeral "15" near its proximal end, indicating that—for the system with which it will be packaged—it will allow a delivery cannula to extend 15 mm beyond the distal end of the corresponding guide cannula. It also includes a numeral "2" near the its distal end indicating that, in one procedure, it should be used as the second of a sequence of spacers. It also includes lengthwise ridges 248 and a series of ribs 247, transverse to its longitudinal axis that may serve as tactile indicia of one of the above-designated qualities or another attribute of the spacer. The longer spacer 260 in FIG. 14 includes a numeral "10" near its proximal end, indicating that—for the system with which it will be packaged—it will allow a delivery cannula to extend 10 mm beyond the distal end of the corresponding guide cannula. It also includes a numeral "1" near the its distal end indicating that, in one procedure, it should be used as the first of a sequence of spacers. The sides of its body have lengthwise ridges 268 (without the transverse ribs) as tactile indicia along its generally cylindrical body 261, which will allow a user to distinguish it by touch alone from, for example, the shorter spacer 240. It will be appreciated that other indicia such as color, texture, and various other visible and/or tactile features may be used within the scope of the present invention. As indicated here, the indicia may include one or more of size data, order of use data, and end orientation data (e.g., proximal versus distal end), and/or other data.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof. For example, while specific reference has been made to vertebroplasty procedures, the devices, systems, and methods in accordance with principles of the present invention are equally applicable to delivering curable material within multiple other bones of a patient.

Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:

1. A cannula device for delivering a curable material, such as bone cement, into bone as part of a curable material delivery system, the device comprising:
  a delivery cannula defining:
    an open, proximal end,
    a deflectable segment opposite the proximal end and terminating in a closed distal end having a blunt tip,
    a lumen extending from the proximal end, at least one side orifice formed adjacent to, and proximally spaced from, the distal end and fluidly connected to the lumen, wherein the deflectable segment forms a curved shape in longitudinal extension and has a shape memory characteristic such that the deflectable segment is configured to assume a longitudinally, substantially straightened form when subjected to a force and naturally revert to the curved shape upon removal of the force, and
    a handle forming a fluid port fluidly coupled to the proximal end;
  a guide cannula including an elongate tubular body extending distally from a guide cannula hub and housing a lumen configured that receives the deflectable segment in a proximal lumen end, the tubular body having a length such that the deflectable segment extends by a first distance from a distal end of the guide cannula when the delivery cannula handle contacts the guide cannula hub; and
  at least one spacer
    including a spacer lumen configured to slidingly receive the delivery cannula, and
    having a longitudinal first spacer length configured to occupy a longitudinal exterior region along the delivery cannula between the delivery cannula handle and the guide cannula hub such that, when spacer lumen is disposed around the delivery cannula between the delivery cannula handle and the guide cannula handle, the deflectable segment may extend beyond the distal end of the guide cannula only up to a second distance that is less than the first distance, wherein the maximum difference between the first distance and the second distance is equal to the first spacer length, and wherein the spacer permits linear non-rotary longitudinal movement of the delivery cannula through the spacer lumen.

2. The cannula device of claim 1, wherein the at least one spacer and the delivery cannula each comprise complementary detent structures configured to engage each other.

3. The cannula device of claim 1, wherein the at least one spacer includes a generally columnar construction and includes an elongate opening along one side and in mechanical communication with the spacer lumen such that the spacer may be mounted to the delivery cannula by passage of a cannula portion through the elongate opening into the spacer lumen while a portion of the delivery cannula is engaged into the guide cannula lumen.

4. The cannula device of claim 1, wherein the at least one spacer comprises indicia selected from visual indicia, tactile indicia, and a combination thereof.

5. The cannula device of claim 4, wherein the indicia comprise at least one of size data, order of use data, and end orientation data.

6. The cannula device of claim 1, wherein the at least one spacer comprises a plurality of spacers.

7. The cannula device of claim 6, wherein each of the plurality of spacers comprises indicia selected from visual indicia, tactile indicia, and a combination thereof, and the indicia of each of the plurality of spacers distinguishes it from all others of the plurality of spacers.

8. The cannula device of claim 1, wherein the at least one spacer is configured to be removable from the region along the delivery cannula between the delivery cannula handle and the guide cannula hub without movement of delivery cannula handle and the guide cannula hub when the deflectable segment of the delivery cannula occupies the guide cannula lumen.

9. A method of injecting curable material to a delivery site within a bone structure, the method comprising:
  providing a delivery cannula defining:
    an open, proximal end,
    a deflectable segment opposite the proximal end having a distal end,
    a lumen extending from the proximal end, wherein the deflectable segment has a shape memory characteristic and naturally assumes a curved shape in longitudinal extension;
  locating a distal tip of a guide cannula within the bone structure;
  inserting the delivery cannula within the guide cannula, characterized by the deflectable segment deflecting to a substantially straightened shape within the guide cannula;
  mounting a first at least one spacer around the delivery cannula in a manner limiting distal longitudinal movement distance of the delivery cannula relative to the guide cannula;
  distally advancing the delivery cannula such that the distal end and at least a portion of the deflectable segment projects distal of the distal tip of the guide cannula by the second distance which is limited by the spacer length of the first at least one spacer, characterized by the portion of the deflectable segment that is distal of the distal tip naturally reverting to the curved shape;
  manipulating the delivery cannula such that at least a portion of the deflectable segment creates a first void in soft body tissue within the bone structure; and
  delivering the curable material to the delivery site wherein the curable material is delivered to the first void.

10. The method of claim 9, wherein the first at least one spacer comprises indicia corresponding to its predetermined length.

11. The method of claim 9, wherein the step of manipulating includes rotating the delivery cannula at least partially about its longitudinal axis.

12. The method of claim 9, further comprising a step of removing the first at least one spacer.

13. The method of claim 12, further comprising steps of:
moving the delivery cannula longitudinally so that the at least a portion of the deflectable segment projects distal of the distal tip of the guide cannula by a third distance different than the second distance; and
manipulating the delivery cannula such that at least a portion of the deflectable segment creates a second void in soft body tissue within the bone structure.

14. The method of claim 12, further comprising steps of:
mounting a second spacer having a second spacer length, different than the first spacer length, around the delivery cannula in a manner limiting distal longitudinal movement distance of the delivery cannula relative to the guide cannula; and
manipulating the delivery cannula such that at least a portion of the deflectable segment creates a second void in soft body tissue within the bone structure.

15. The method of claim 14, further comprising a step of delivering the curable material to the second void.

16. The method of claim 9, further comprising the steps of:
measuring the bone structure; and
selecting the first at least one spacer based upon a desirable length thereof for directing the blunt tip of the delivery cannula to a desired location within the bone structure.

17. A kit for performing a vertebroplasty procedure, the kit comprising:
a delivery cannula including:
a proximal end handle including a proximal fluid port configured for connection with a curable material delivery device,
an elongate tubular member extending distally from the handle and including a deflectable segment opposite the proximal end handle, the deflectable segment terminating in a closed distal end having a blunt tip, and
a lumen extending through the tubular member from the proximal end handle, at least one side orifice formed adjacent to, and proximally spaced from, the distal end and fluidly connected to the lumen, wherein the deflectable segment forms a curved shape in longitudinal extension and has a shape memory characteristic such that the deflectable segment is configured to assume a longitudinally, substantially straightened form when subjected to a force and naturally revert to the curved shape upon removal of the force;
a guide cannula including:
an elongate tubular body extending distally from a guide cannula hub and housing a guide lumen configured to receive the deflectable segment in a proximal end, the tubular body configured with a length such that the deflectable segment extends by a first distance from a distal end of the guide cannula when the delivery cannula handle contacts the guide cannula hub; and
at least one spacer including
a spacer length and
a central lumen in open communication with an elongate side aperture that is mountable upon the delivery cannula when the elongate tubular member of the delivery cannula is engaged into the elongate tubular body of the guide cannula,
the central lumen providing for longitudinal non-rotary movement of the delivery cannula through the central lumen,
where the spacer length is configured to occupy a region along the delivery cannula between the delivery cannula handle and the guide cannula hub such that the deflectable segment may extend beyond the distal end of the guide cannula by a second distance that is less than the first distance,
wherein the difference between the first distance and the second distance is less than or equal to the spacer length.

18. The kit of claim 17, wherein the at least one spacer comprises a second spacer having a different length than a first at least one spacer.

19. The kit of claim 18, wherein the spacers each comprise indicia differentiating them from each other.

20. An intraosseous, curable material delivery system for delivering a curable material such as bone cement to a delivery site within bone, the system comprising:
a delivery cannula defining:
an open, proximal end,
a deflectable segment opposite the proximal end and terminating in a distal end, and
a lumen extending from the proximal end, wherein the deflectable segment has a shape memory characteristic and assumes a curved shape in longitudinal extension;
a guide cannula defining an inner diameter greater than an outside diameter of the delivery cannula and having an open distal tip; and
a spacer configured to control longitudinal distance of engagement of the delivery cannula with the guide cannula, wherein the spacer is engaged around and is laterally removable from the delivery cannula when the delivery cannula is engaged into the inner diameter of the guide cannula;
wherein the deflectable segment is configured to be deflectable to a substantially straightened shape such that the delivery cannula is slidable within the guide cannula, and to naturally revert to the curved shape when extended distal the distal tip for delivery of a curable material within implantation site via the distal end; and
wherein the delivery cannula is smoothly slidable within the guide cannula.

* * * * *